US009435021B2

(12) United States Patent
Thompson et al.

(10) Patent No.: US 9,435,021 B2
(45) Date of Patent: Sep. 6, 2016

(54) CO-DEPOSITION METHODS FOR THE FABRICATION OF ORGANIC OPTOELECTRONIC DEVICES

(75) Inventors: Mark E. Thompson, Ewing, NJ (US); Zhiwei Liu, Ewing, NJ (US); Chao Wu, Ewing, NJ (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1310 days.

(21) Appl. No.: 13/193,036

(22) Filed: Jul. 28, 2011

(65) Prior Publication Data

US 2012/0045862 A1   Feb. 23, 2012

Related U.S. Application Data

(60) Provisional application No. 61/400,505, filed on Jul. 29, 2010.

(51) Int. Cl.
C23C 14/14 (2006.01)
C07F 1/08 (2006.01)
C23C 14/12 (2006.01)
C07F 1/00 (2006.01)
H01L 51/00 (2006.01)
C09K 11/06 (2006.01)
H01L 51/50 (2006.01)

(52) U.S. Cl.
CPC ............... *C23C 14/12* (2013.01); *C07F 1/005* (2013.01); *H01L 51/001* (2013.01); *H01L 51/0091* (2013.01); *C09K 11/06* (2013.01); *C09K 2211/1007* (2013.01); *C09K 2211/1029* (2013.01); *C09K 2211/1048* (2013.01); *C09K 2211/188* (2013.01); *H01L 51/5016* (2013.01)

(58) Field of Classification Search
CPC ...................................................... C09K 11/06
USPC ............................................................ 546/2
See application file for complete search history.

(56) References Cited

U.S. PATENT DOCUMENTS 4,769,292 A   9/1988 Tang et al.
5,061,569 A   10/1991 VanSlyke et al.
(Continued)

FOREIGN PATENT DOCUMENTS

EP   0650955   5/1995
EP   1725079   11/2006
(Continued)

OTHER PUBLICATIONS

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).
(Continued)

*Primary Examiner* — Francisco Tschen
(74) *Attorney, Agent, or Firm* — Duane Morris LLP

(57) ABSTRACT

A method for fabricating an OLED by preparing phosphorescent metal complexes in situ is provided. In particular, the method simultaneously synthesizes and deposits copper (I) complexes in an organic light emitting device. Devices comprising such complexes may provide improved photoluminescent and electroluminescent properties.

20 Claims, 15 Drawing Sheets

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,198,217 B1 * | 3/2001 | Suzuki | H01L 51/5237 313/504 |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0129978 A1 | 6/2005 | Nakashima et al. | |
| 2005/0221115 A1 * | 10/2005 | Tsuboyama et al. | 428/690 |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0066228 A1 * | 3/2006 | Antoniadis et al. | 313/506 |
| 2006/0202194 A1 | 9/2006 | Jeong et al. | |
| 2006/0220004 A1 * | 10/2006 | Stossel et al. | 257/40 |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0103060 A1 * | 5/2007 | Itoh | C07D 213/06 313/504 |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 10/2009 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008101842 | 8/2008 |
| WO | WO 2008132085 | 11/2008 |
| WO | WO 2009/000673 | 12/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2008506746 | 5/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinotinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

(56) References Cited

OTHER PUBLICATIONS

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).
Gao, Zhiqiang et al., "Bright-Blue Electroluminescence From a Silyl-Substituted ter-(phenylene-vinylene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).
Hung, L.S. et al., "Anode Modification in Organic Light-Emitting Diodes by Low-Frequency Plasma Polymerization of $CHF_3$," *Appl. Phys. Lett.*, 78(5):673-675 (2001).
Ikai, Masamichi and Tokito, Shizuo, "Highly Efficient Phosphorescence From Organic Light-Emitting Devices with an Exciton-Block Layer," *Appl. Phys. Lett.*, 79(2)156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *App. Phys. Lett.*, 78(11):1622-1624 (2001).
Wong, Keith Man-Chung et al., A Novel Class of Phosphorescent Gold(III) Alkynyl-Based Organic Light-Emitting Devices with Tunable Colour, *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2-α]pyricline Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota,Yasuhiko, "5,5'-Bis(dimesitylboryl)-2,2'-bithiophene and 5,5"-Bis(dimesitylboryl)-2,2':5',2"-terthlophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al., 1,2,4-Triazole Derivative as an Electron Transport Layer in Organic Electroluminescent Devices, *Jpn. J. Appl. Phys.*, 32:L917-L920 (1993).
Van Slyke, S. A. et al., "Organic Electroluminescent Devices with Improved Stability," *Appl. Phys. Lett.*, 69(15):2160-2162 (1996).
Guo, Tzung-Fang et al., "Highly Efficient Electrophosphorescent Polymer Light-Emitting Devices," *Organic Electronics*, 1:15-20 (2000).
Pallis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electraluminescence," *Synthetic Metals*, 91:209-215 (1997).
U.S. Appl. No. 61/400,505, filed Jul. 29, 2010.
Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 3, 4-6 (1999).
Lamansky et al., *Journal of the American Chemical Society* 2001,123, (18), 4304-4312.
Adachi et al., S. R, *Journal of Applied Physics* 2001, 90, (10), 5048-5051.
Armaroli et al., *Photochemistry and Photophysics of Coordination Compounds*, (2007), 280, 69-115.
Kyle et al., *Journal of the American Chemical Society* 1991, 113, (8), 2954-2965.
Manbeck et al., *Inorganic Chemistry* 2010, 49, (6),2834-2843.
Tard, et al., *Chemistry of Materials* 2008, 20, (22), 7010-7016.
Vitale, et al., *Coordination Chemistry Reviews* 2001, 219, 3-16.
Ford, P. C., *Coordination Chemistry Reviews* 1994, 132, 129-140.
Ryu, et al., *Inorganic Chemistry* 1993, 32, (6), 869-874.
Raston, et al., *Journal of the Chemical Society-Dalton Transactions* 1976, (21), 2153-2156.
Rath, et al., *Journal of the Chemical Society-Dallon Transactions* 1986, (II), 2449-2453.
Dyason, et al., *Inorganic Chemistry* 1985,24, (12),1957-1960.

(56) References Cited

OTHER PUBLICATIONS

Eitel et al, "Structural Isomers of Coper(I) Iodide Pyridine and their Luminescence Properties, Synthesis and Crystal Structure of a New Modification of CuI NC.sub.5 NC.sub.5 H.sub.5", Z. Naturforsch (1980), pp. 1247-1253. (English language abstract on p. 3).
De Angelis, et al., *Inorganic Chemistry* 2006,45, (26),10576-10584.
Zhang, et al., *Advanced Materials* 2004, 16, (5), 432-+.
Che, et al., *Applied Physics Letters* 2006, 89, (10).
Su, et al., *Applied Physics Letters* 2006, 88, (21).
Tsuboyama, et al., *Inorganic Chemistry* 2007,46, (6),1992-2001.
Zhiwei Liu et al: "A Codeposition Route 1-23 to CuI-Pyridine Coordination Complexes for Organic light-Emitting Diodes", Journal of the American Chemical Society, vol. 133, No. 11, Mar. 23, 2011, pp. 3700-3703
Ford et al., "Photoluminescence Properties of Multinuclear Copper(I) Compounds", Chemical Reviews, vol. 99, No. 12, Dec. 1, 1999, pp. 3625-3648.
The International Search Report in PCT/US2011/045770 application.

* cited by examiner

CO-DEPOSITION METHODS FOR THE FABRICATION OF ORGANIC OPTOELECTRONIC DEVICES

This application claims priority to U.S. Provisional Application Ser. No. 61/400,505, filed Jul. 29, 2010, the disclosure of which is herein expressly incorporated by reference in its entirety.

This invention was made with government support under DE-FC26-08NT01585 and DE-FG02-07ER84809 awarded by the Department of Energy. The government has certain rights in the invention.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to phosphorescent complexes, and their use in organic light emitting devices (OLEDs). More particularly, the invention relates to a method for simultaneously synthesizing and depositing phosphorescent copper (I) complexes for fabrication of an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the following structure:

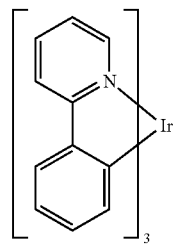

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Methods for depositing a phosphorescent complex in situ are provided. The method comprises reacting one or more of a metal complex having the formula $MX_n$ and one or more of a ligand selected from $L_1$, $L_2$, and $L_3$ to form a phosphorescent complex having the formula $(L_1)_a(L_2)_b(L_3)_c(MX_p)_m$. The one or more metal complexes having the formula $MX_n$ and the one or more ligands $L_1$, $L_2$, and $L_3$ are thermally vacuum deposited in combination over a substrate, wherein the reaction is completed to obtain the phosphorescent complex.

M is a transition metal or lanthanide. X is alkyl, aryl, F, Cl, Br, I, SCN, OCN, CN, OR, and SR or combinations thereof. R is alkyl or aryl. n is 1-10. Preferably, n is 1-3. p is equal to $[n-(a \cdot a')+(b \cdot b')+(c \cdot c')]$. m is 1-6. Preferably, m is 2. Each of $L_1$, $L_2$, and $L_3$ is independently a mono-, di-, tri- or polydentate ligand. Each of a, b, and c may represent mono, bis or tris ligand coordination. a is 1-10, b is 0-9, and c is 0-9. a' is the number of coordination sites of $L_1$. b' is the number of coordination sites of $L_2$. c' is the number of coordination sites of $L_3$. $[p+(a \cdot a')+(b \cdot b')+(c \cdot c')]$ is equal to n.

Preferably, the metal complex is copper (I). More preferably, the metal complex is CuI.

At least one of the ligands $L_1$, $L_2$, and $L_3$ may be a neutral ligand. In one aspect, at least one of $L_1$, $L_2$, and $L_3$ is a neutral ligand that is coordinated to the Cu through a C, N, O, P or S atom. Preferably, at least one of $L_1$, $L_2$, and $L_3$ is a neutral ligand that is coordinated to the Cu through a N atom.

In another aspect, each of $L_1$, $L_2$, and $L_3$ is a neutral ligand that is coordinated to the Cu through a C, N, O, P or S atom. Preferably, each of $L_1$, $L_2$, and $L_3$ is a neutral ligand that is coordinated to the Cu through a N atom.

In yet another aspect, at least one of $L_1$, $L_2$, and $L_3$ is selected from the group consisting of:

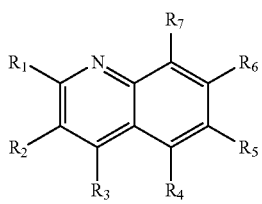

-continued

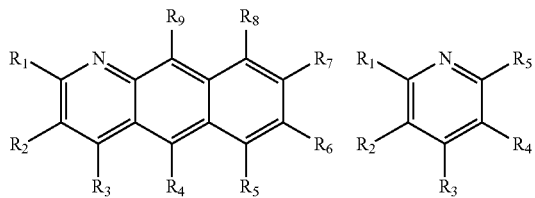

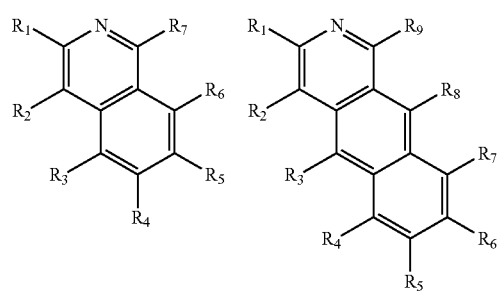

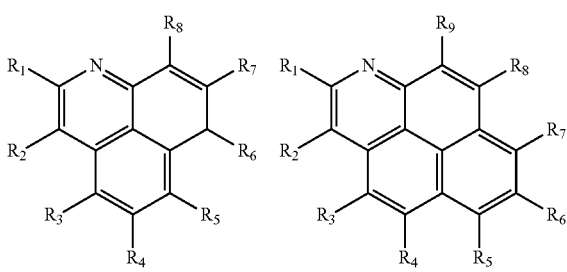

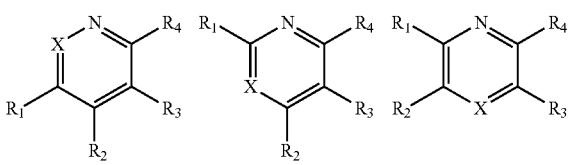

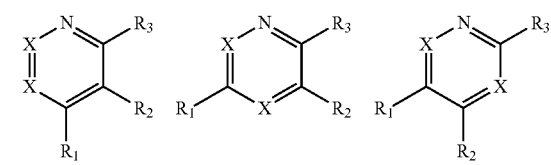

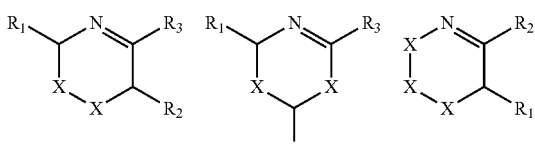

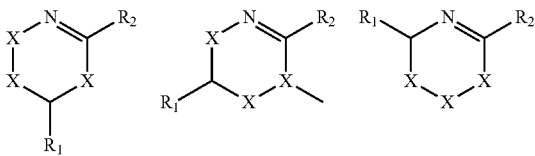

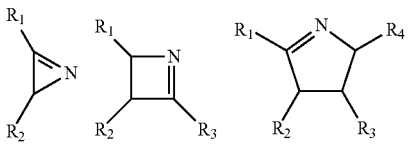

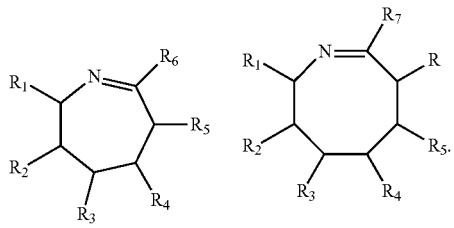
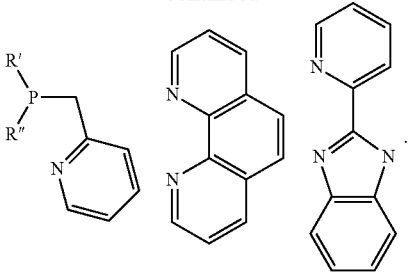

X is S, O, or NR. R, $R_1$, $R_2$, $R_3$, $R_4$, $R_5$, $R_6$, $R_7$, $R_8$ and $R_9$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, phosphino, and combinations thereof. The ligand is coordinated to the metal M via at least atom of the ligand.

Specific examples of ligands $L_1$, $L_2$, and $L_3$ are provided. In one aspect, at least one of $L_1$, $L_2$, and $L_3$ is selected from the group consisting of:

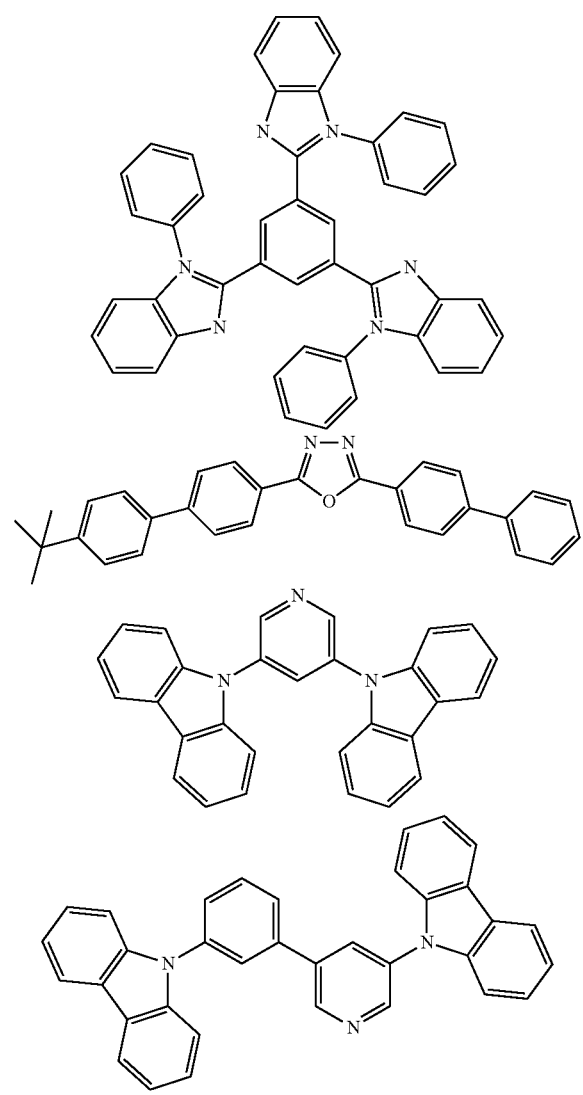

R' and R" are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

Alternatively, at least one of the ligands $L_1$, $L_2$, and $L_3$ may be a charged ligand. In one aspect, at least one of $L_1$, $L_2$, and $L_3$ is a charged ligand having the formula:

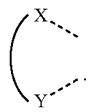

Y and X are independently selected from the group consisting of C, N, O, P and S.

In another aspect,

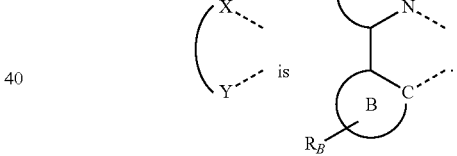

A and B are each independently a 5 or 6-membered aromatic or heteroaromatic ring. A-B represents a bonded pair of aromatic or heteroaromatic rings coordinated to the metal via a nitrogen atom on ring A and an sp$^2$ hybridized carbon atom on ring B. Each of $R_A$ and $R_B$ may represent mono, di, tri, or tetra substituents. Each of $R_A$ and $R_B$ substituents are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

The phosphorescent complex obtained from the method may be homoleptic or heteroleptic. In one aspect, b is 0 and c is 0. In another aspect, at least one of b and c is equal to 1.

In one aspect, p is 0.

Specific examples of the phosphorescent complex obtained from the method are provided. In one aspect, the phosphorescent complex is selected from the group consisting of CuI:TPBi, CuI:PBD, or CuI:mCPy.

In one aspect, the one or more metal complexes having the formula $MX_n$ and the one or more ligands $L_1$, $L_2$, and $L_3$ are deposited by solution processing. In another aspect, the one or more metal complexes having the formula $MX_n$ and the one or more ligands $L_1$, $L_2$, and $L_3$ are deposited by thermal evaporation.

In one aspect, the one or more metal complexes $MX_n$ is mixed with an organic solvent to form a first solution and at least one of $L_1$, $L_2$, and $L_3$ is mixed with an organic solvent to form a second solution, prior to depositing over the substrate, and then the first solution and the second solution are deposited in combination over the substrate.

In another aspect, the method further comprises providing a first electrode disposed over the substrate, depositing the one or more metal complexes having the formula $MX_n$ and the ligand L on the first electrode, and depositing a second electrode. Preferably, the first electrode is an anode and the second electrode is a cathode.

In another aspect, the method further comprises providing a first electrode disposed over the substrate, providing an organic layer disposed over the first electrode, depositing the one or more metal complexes having the formula $MX_n$ and the ligand L on the first electrode, and depositing a second electrode. Preferably, the first electrode is an anode and the second electrode is a cathode.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
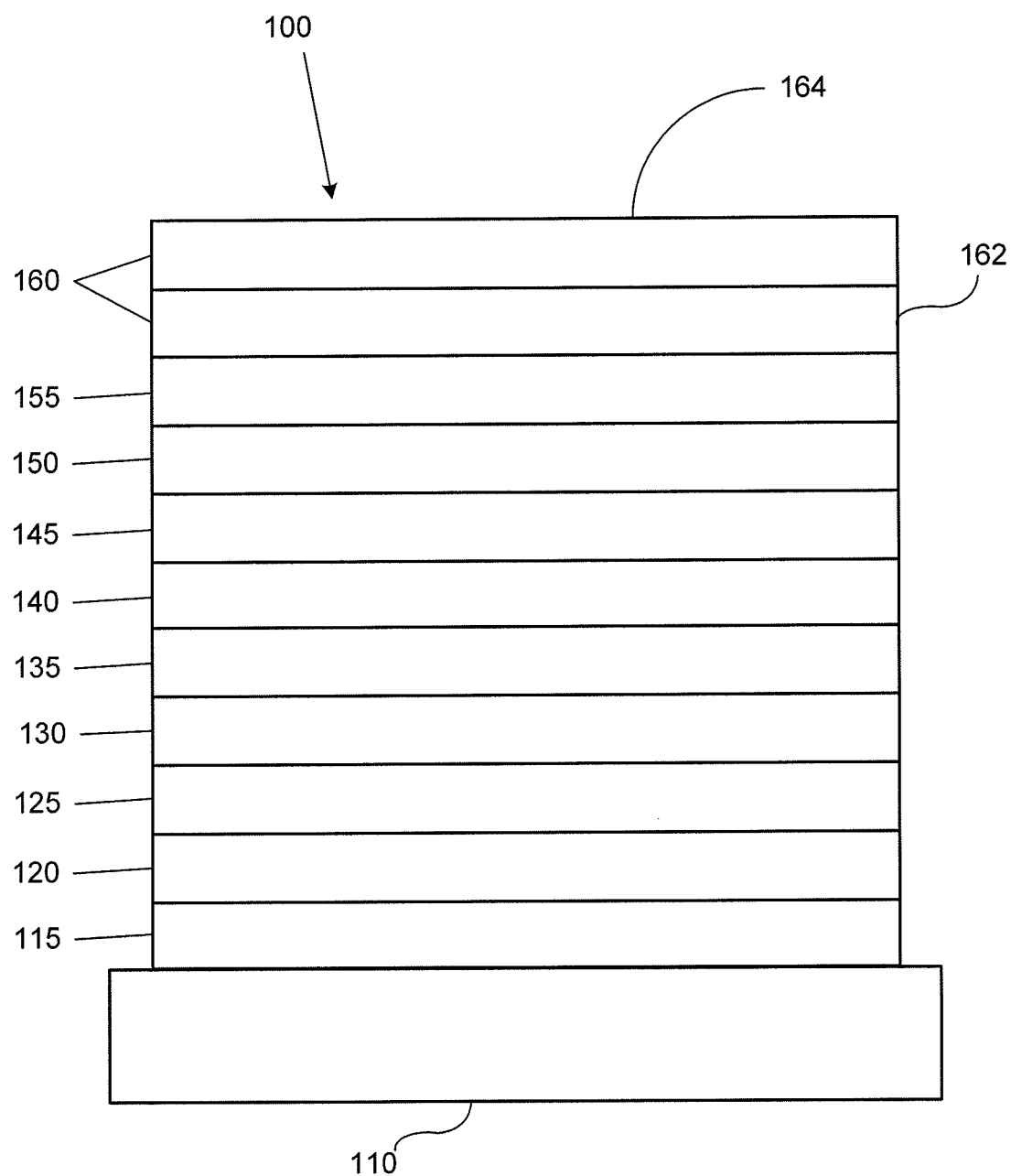
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
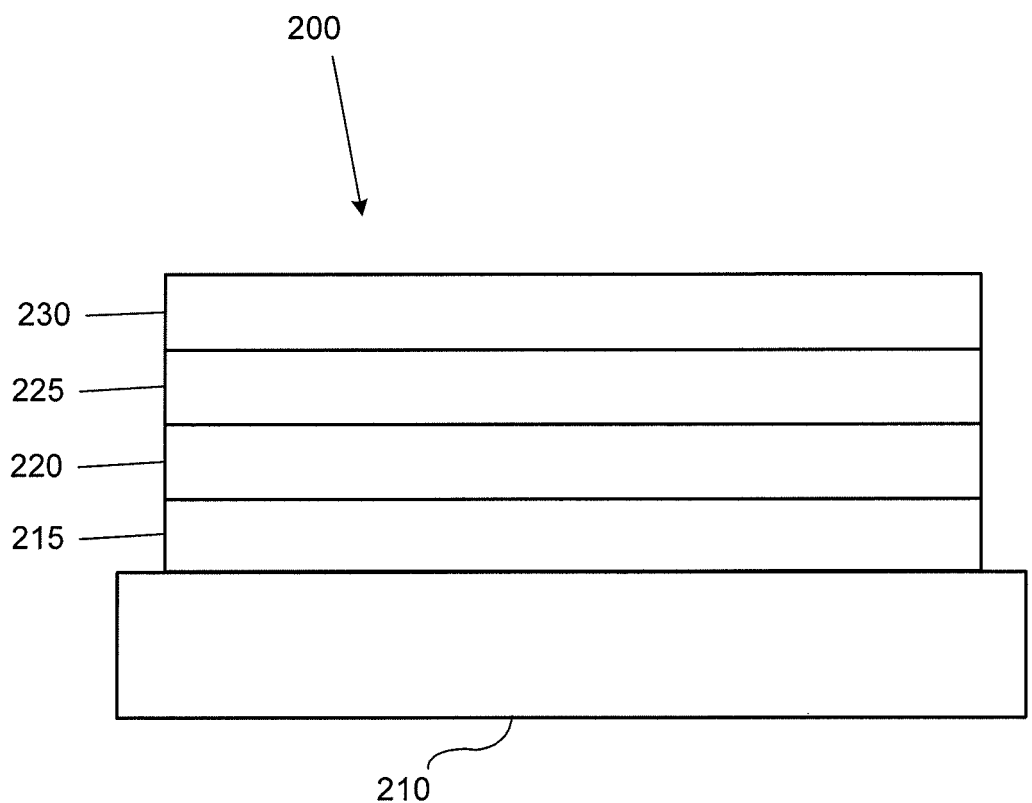
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A wide range of phosphorescent emissive materials for application to OLEDs and other optoelectronic devices have been reported. These materials are typically synthesized and purified as crystalline material, prior to their incorporation into a device via thermal evaporation. While phosphorescent copper complexes can be synthesized and purified as crystalline materials, they decompose on attempts to deposit them by thermal evaporation. Phosphorescent copper complexes may be desirable for use in OLEDs, but their use has been limited because of these sublimation problems.

Herein, a new method for the fabrication of a phosphorescent complex is provided. Phosphorescent emitters are prepared in situ by co-depositing a ligand and a metal complex to form a film. In particular, the method may involve the co-deposition of CuI and one or more organic ligands to form the phosphorescent complex. Particularly desirable phosphorescent complexes that can be obtained using this method have the general formula $(CuI)_yL_z$, with $(CuI)_y$ cluster cores.

Figure 3:
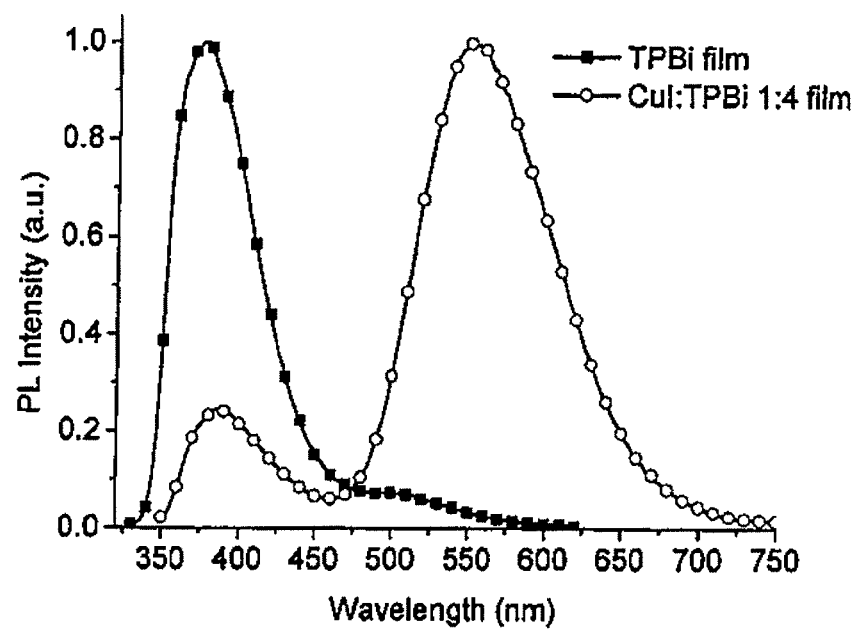
FIG. 3 shows photoluminescent spectra of spin cast TPBi and CuI:TPBi films at a 1:4 ratio.
Figure 4:
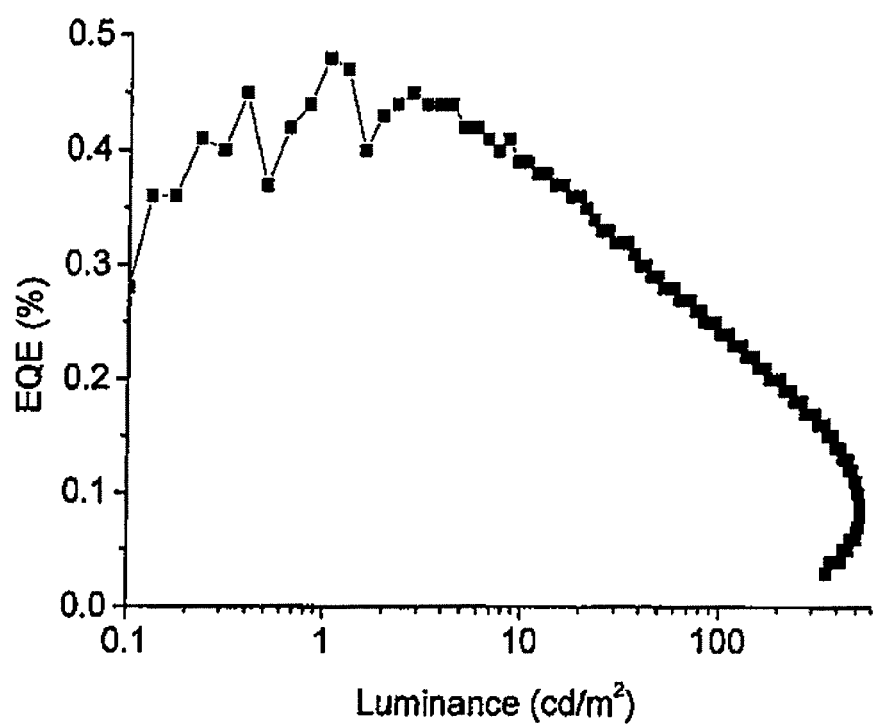
FIG. 4 shows the external quantum efficiency-luminance curve for a device having the structure ITO/NPD (1000 Å)/CuI:TPBi (1:1.7, 100 Å)/TPBi (500 Å)/LiF (10 Å)/Al (1000 Å), where the CuI:TPBi layer was made by co-depositing CuI and TPBi in vacuum chamber.
Figure 5:
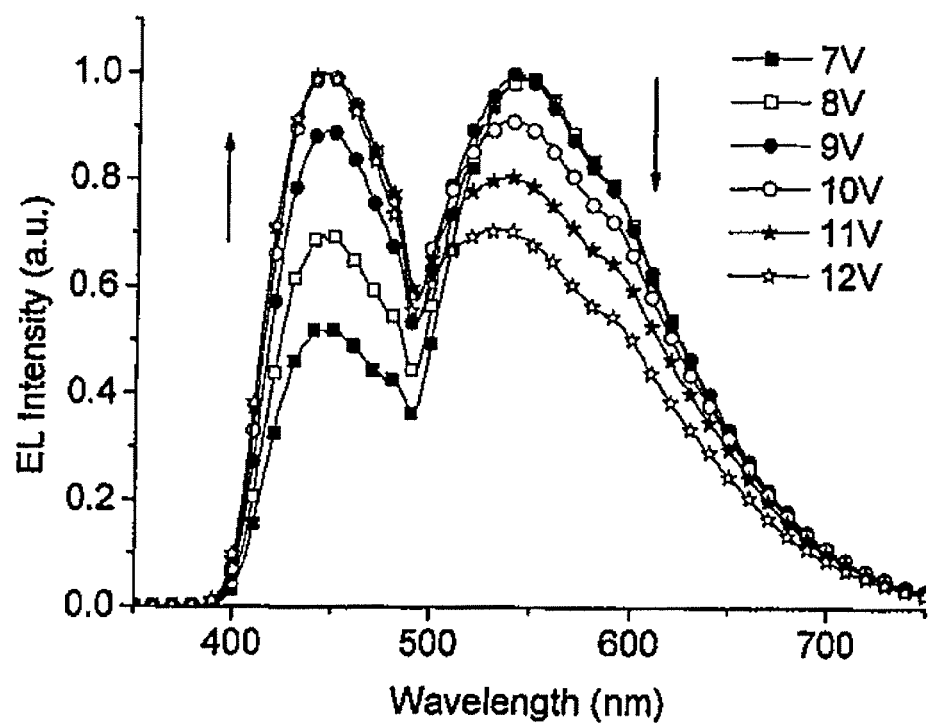
FIG. 5 shows the electroluminescent spectra for a device having the structure ITO/NPD (1000 Å)/CuI:TPBi (1:1.7, 100 Å)/TPBi (500 Å)/LiF (10 Å)/Al (1000 Å) under different voltages
Figure 6:
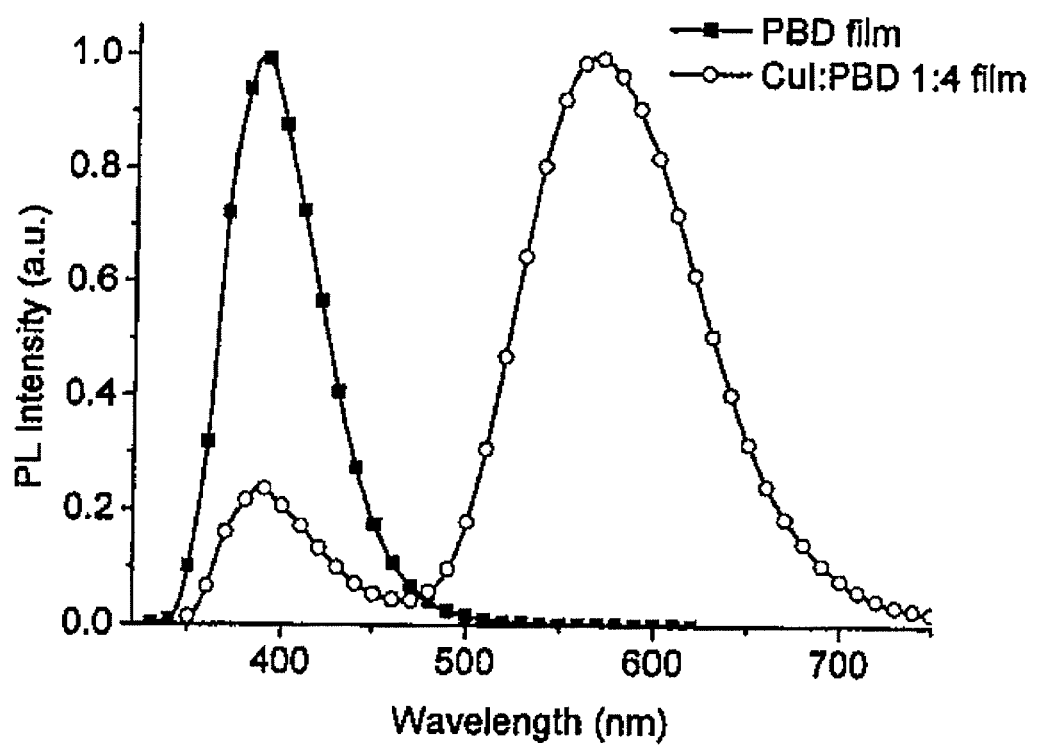
FIG. 6 shows the photoluminescent spectra of spin cast PBD and CuI:PBD films at a 1:4 ratio.
Figure 7:
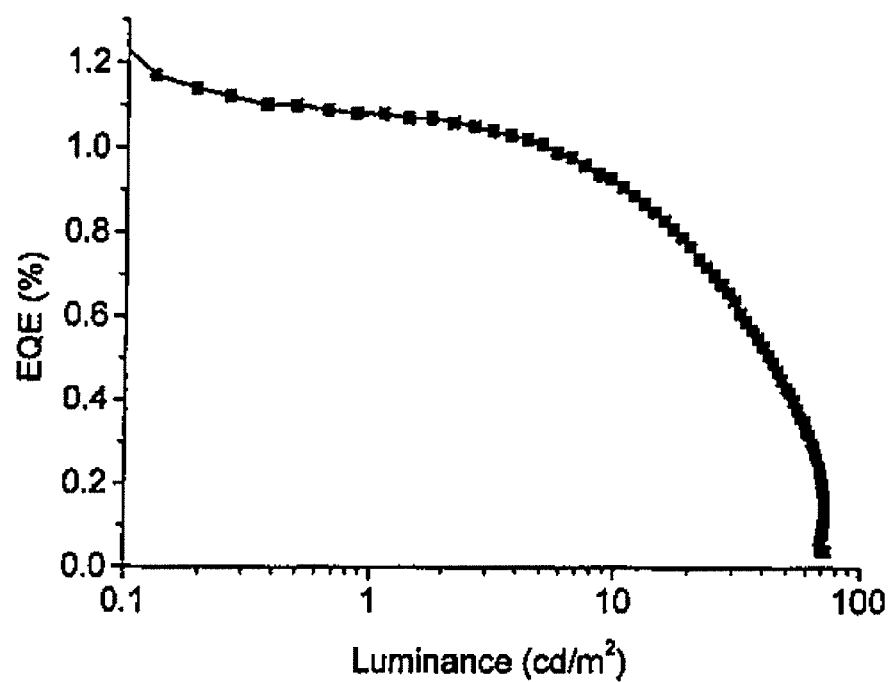
FIG. 7 shows the external quantum efficiency-luminance curve for a device having the structure ITO/NPD (1000 Å)/CuI:PBD (1:1, 100 Å)/PBD (500 Å)/LiF (10 Å)/Al (1000 Å), where the CuI:PBD layer was made by co-depositing CuI and PBD in vacuum chamber.
Figure 8:
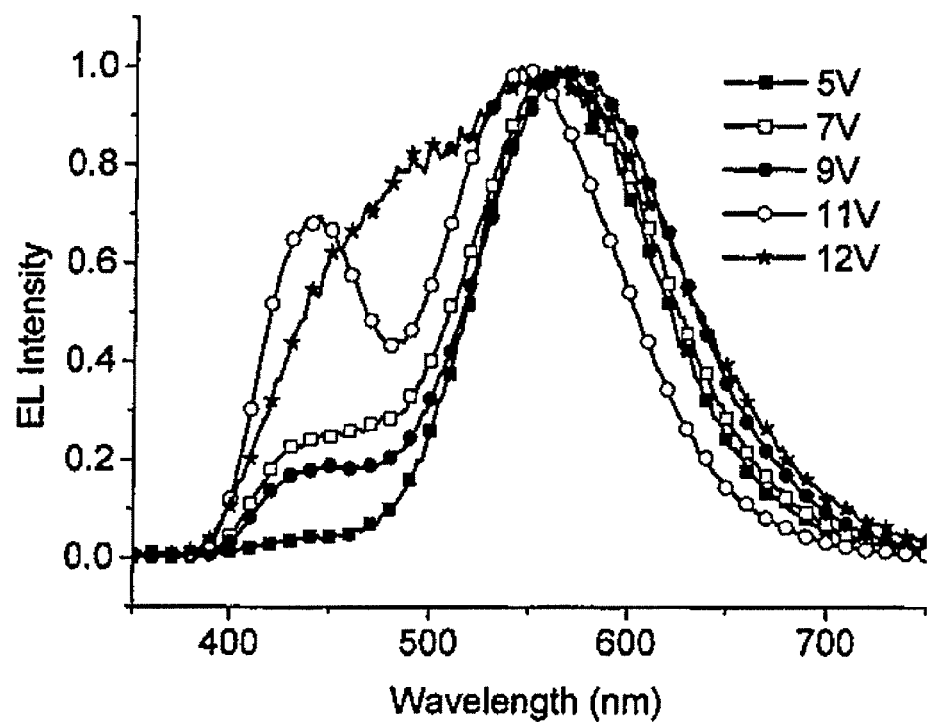
FIG. 8 shows the electroluminescent spectra for a device having the structure ITO/NPD (1000 Å)/CuI:PBD (1:1, 100 Å)/PBD (500 Å)/LiF (10 Å)/Al (1000 Å) under different applied voltages.
Figure 12:
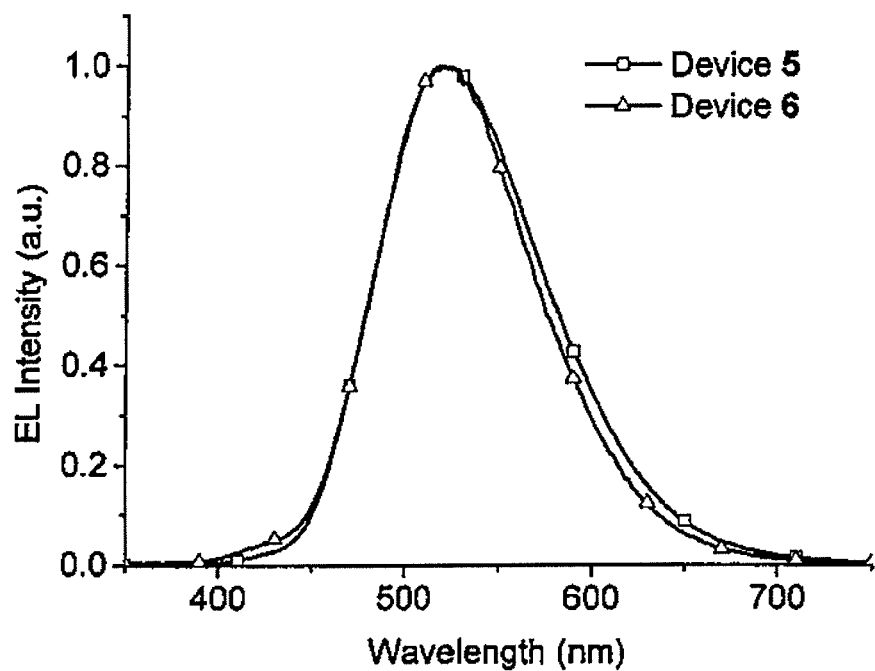
FIG. 12 shows the electroluminescent spectra of devices 5 and 6 at 8 V.
Figure 13:
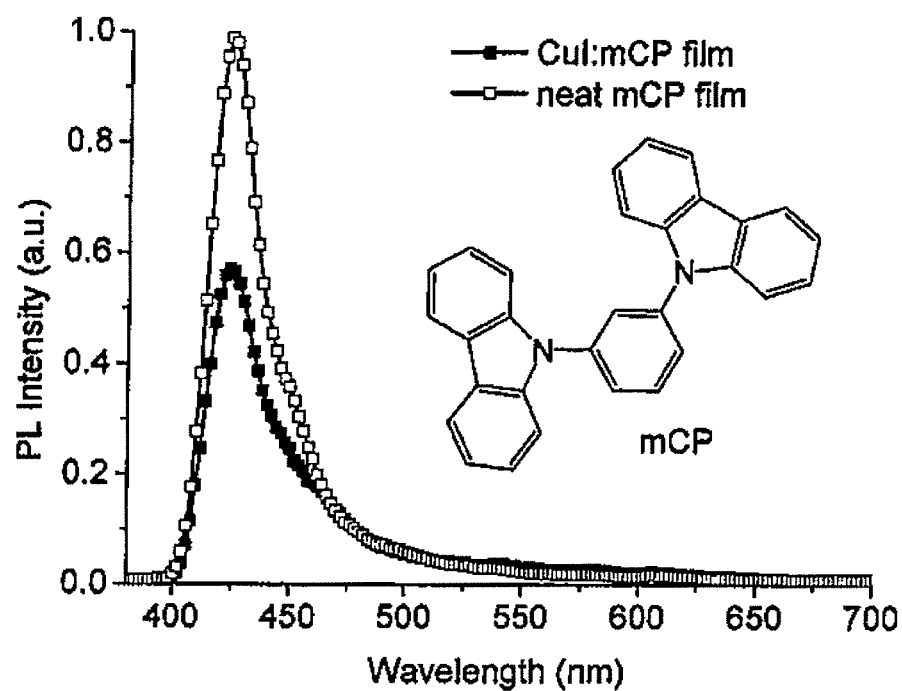
FIG. 13 shows the photoluminescent spectra of CuI:mCP and neat mCP films.
Figure 14:
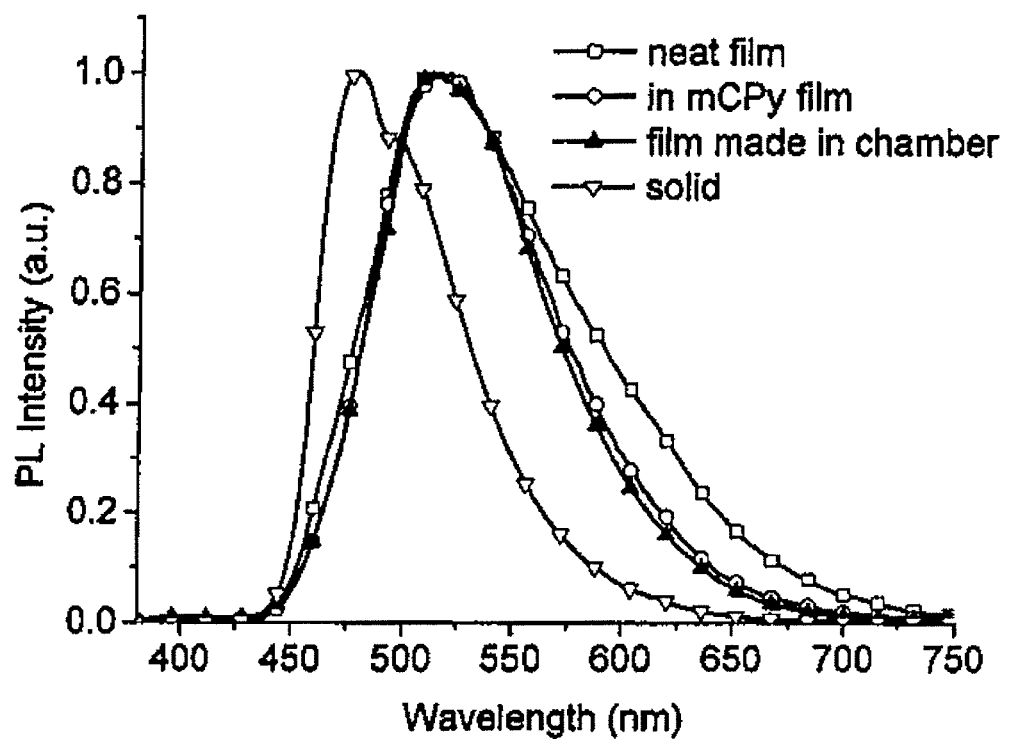
FIG. 14 shows the photoluminescent spectra of model complex A in solid, neat film, A:mCPy film, and in chamber co-deposited CuI:mCPy film. The former two films were made by spin coating of sample in $CH_3CN+CH_2Cl_2$ solution.
Figure 15:
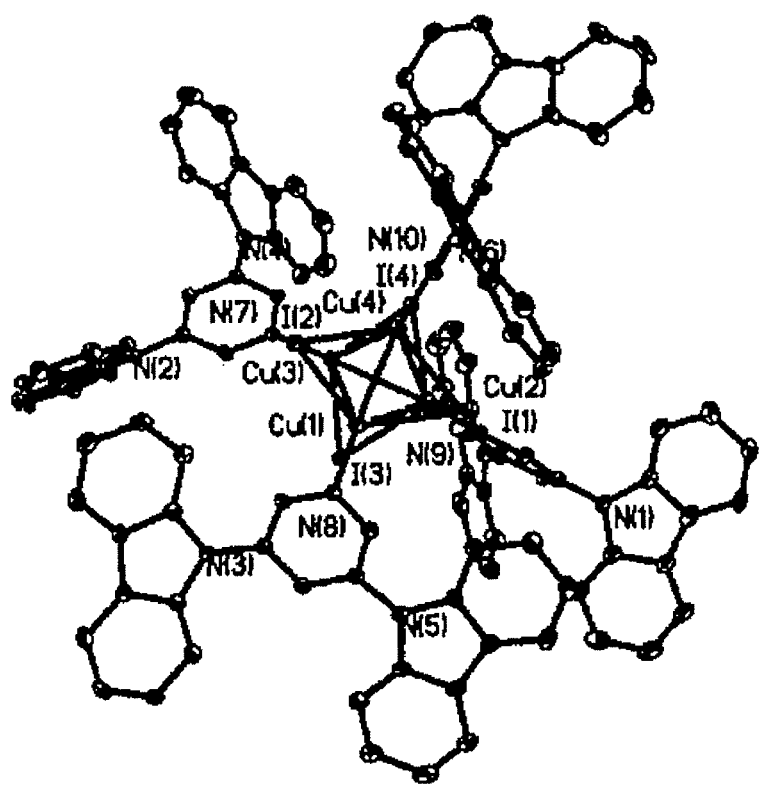
FIG. 15 shows an ORTEP drawing of the model complex B with ellipsoids at the 30% probability level. Hydrogen and solvents are omitted for clarity.

The organic ligands that may be used in this method can include a wide range of materials, provided they are sufficiently Lewis basic enough to coordinate to the metal, and in particular Cu ions. Examples of suitable ligands may include, but are not limited to, 2,2',2"-(1,3,5-benzinetriyl)-tris(1-phenyl-1-H-benzimidazole) (TPBi), 2-(4-biphenylyl)-5-(4-tert-butylphenyl)-1,3,4-oxadiazole (PBD), 3,5-di(9H-carbazol-9-yl)pyridine (mCPy), or 1,3-bis(carbazol-9-yl)benzene (mCP). FIGS. 3-5 show electroluminescent and photoluminescent data for CuI:TPBi. FIGS. 6-8 show electroluminescent and photoluminescent data for CuI:PBD. FIGS. 9-12 and 14 show electroluminescent and photoluminescent data for CuI:mCPy. FIG. 13 shows electroluminescent and photoluminescent data for CuI:mCP. FIG. 15 shows the structure of $Cu_4I_4(mCPy_4)\cdot 3CH_2Cl_2$, or the model complex B.

Phosphorescent complexes made by the method provided herein are suitable for use in an emissive layer of an OLED. For example, the methods provided herein were used to prepare OLEDs with a phosphorescent copper complex as the emitting center and the devices demonstrated an EQE value of 4.4%.

Novel methods are provided for in situ formation of phosphorescent compounds, particularly copper (I) complexes, by co-depositing one or more metal complexes and one or more ligands under vacuum. These methods may be used to fabricate OLEDs containing phosphorescent copper (I) complexes. The co-deposition method may also be used for in situ formation of emissive complexes containing other metals or metal halides suitable for use as an emissive layer in OLEDs.

Over the past ten years, tremendous improvements in phosphorescent organic light emitting diodes (PHOLEDs) have been achieved with the help of emissive iridium-based complexes. Generally, iridium complexes possess good thermal stability, suitable for evaporation under vacuum, and potentially 100% internal quantum efficiency. fac-tris(2-phenylpyridine)iridium [Ir(ppy)3] and bis(2-phenylpyridine)(acetylacetonate)iridium [Ir(ppy)$_2$(acac)] are two examples of such iridium complexes. See, Lamansky, S.; Djurovich, P.; Murphy, D.; Abdel-Razzaq, F.; Lee, H. E.; Adachi, C.; Burrows, P. E.; Forrest, S. R.; Thompson, M. E., *Journal of the American Chemical Society* 2001, 123, (18), 4304-4312; Adachi, C.; Baldo, M. A.; Thompson, M. E.; Forrest, S. R, *Journal of Applied Physics* 2001, 90, (10), 5048-5051.

However, iridium is low in natural abundance and expensive, prohibiting PHOLEDs from being widely used in applications, such as displays and solid state lighting. As a result, there has been an increasing interest in luminescent copper(I) complexes and their application in PHOLEDs, because copper(I) complexes are the largest class of phosphorescent compounds with a relatively abundant, cheap, and environmentally friendly metal element. See, Arrnaroli, N.; Accorsi, G.; Cardinali, F.; Listorti, A., *Photochemistry and Photophysics of Coordination Compounds* 12007, 280, 69-115.

Among the luminescent copper(I) complexes, copper(I) iodide based complexes are well known for their rich structure and photophysical behavior. See, Ford, P. C.; Carlati, E.; Bourassa, J., *Chemical Reviews* 1999, 99, (12), 3625.3647; Kyle, K. R.; Ryu, C. K.; Dibenedetto, J. A.; Ford, P. C., *Journal of the American Chemical Society* 1991, 113, (8), 2954-2965; Manbeck, G. F.; Brennessel, W. W.; Evans, C. M.; Eisenberg, R., *Inorganic Chemistry* 2010, 49, (6), 2834-2843; Tard, C.; Perruchas, S.; Maron, S.; Le Goff, X. F.; Guillen, F.; Garcia, A.; Vigneron, J.; Elcheberry, A.; Gacoin, T.; Boilot, J. P., *Chemistry of Materials* 2008, 20, (22), 7010-7016; Vitale, M.; Ford, P. C., *Coordination Chemistry Reviews* 2001, 219, 3-16; Ford, P. C., *Coordination Chemistry Reviews* 1994, 132, 129-140; Ryu, C. K.; Vitale, M.; Ford, P. C., *Inorganic Chemistry* 1993, 32, (6), 869-874. For example, structures ranging from the mononuclear CuI(3-Mepy)$_3$ to polynuclear [Culpy]$_\infty$ have been prepared by combining copper(I) iodide and pyridine-based ligands at different ratios. See, Raslon, C. L.; White, A. H., *Journal of the Chemical Society-Dalton Transactions* 1976, (21), 2153-2156; Rath, N. P.; Maxwell, 1. L.; Holl, E. M., *Journal of the Chemical Society-Dallon Transactions* 1986, (II), 2449-2453; Dyason, J. C.; Healy, P. C.; Pakawatchai, C.; Patrick, V. A.; While, A. H., *Inorganic Chemistry* 1985, 24, (12), 1957-1960; Eitel, E.; Oelkrug, D.; Hiller, W.; Strahle, J., *Zeitschrijt Fur Naturforschung Section B-a Journal of Chemical Sciences* 1980, 35, (10), 1247-1253. Excited states in these complexes have been proposed to be halide-to-ligand charge transfer (XLCT), metal-to-ligand charge transfer (MLCT), and/or halide-to-metal charge transfer (XMCT) based on experimental and computational work. See, De Angelis, F.; Fantacci, S.; Sgamellotti, A.; Cariati, E.; Ugo, R.; Ford, P. C., *Inorganic Chemistry* 2006, 45, (26), 10576-10584. Generally, copper(I) iodide based complexes, especially those with a pyridine derivative as ligand, are highly emissive at room temperature regardless of structure and nature of excited state.

To date, a number of copper complexes with high photoluminescence quantum yield (PLQY) have been reported. However, studies on their application in OLEDs is limited. Most copper complexes are not sublimable, and, hence, are incapacitated from standard vacuum thermal evaporation based OLED fabrication methods. See, Zhang, Q. S.; Zhou, Q. G.; Cheng, Y. X.; Wang, L. x.; Ma, D. G.; Jing, X. B.; Wang, F. S., *Advanced Materials* 2004, 16, (5), 432-+; Che, G. B.; Su, Z. S.; Li, W. L.; Chu, B.; Li, M. T.; Hu, Z. Z.; Zhang, Z. Q., *Applied Physics Letters* 2006, 89, (10); Su, Z. S.; Che, G. B.; Li, W. L.; Su, W. M.; Li, M. T.; Chu, B.; Li, B.; Zhang, Z. Q.; Hu, Z. Z., *Applied Physics Letters* 2006, 88, (21); Tsuboyama, A.; Kuge, K.; Furugori, M.; Okada, S.; Hoshino, M.; Veno, K., *Inorganic Chemistry* 2007, 46, (6), 1992-2001.

Methods for depositing a phosphorescent complex in situ are provided. The method comprises reacting one or more metal complexes having the formula $MX_n$ and one or more of a ligand selected from $L_1$, $L_2$, and $L_3$ to form a phosphorescent complex having the formula $(L_1)_a(L_2)_b(L_3)_c(MX_p)_m$. The one or more metal complexes having the formula $MX_n$ and the one or more ligands $L_1$, $L_2$, and $L_3$ are thermally vacuum deposited in combination over a substrate, wherein the reaction is completed to obtain the phosphorescent complex.

M is a transition metal or lanthanide. X is alkyl, aryl, F, Cl, Br, I, SCN, OCN, CN, OR, and SR or combinations thereof, R is alkyl or aryl. m is 1-6. Preferably, m is 2. n is 1-10. Preferably, n is 1-3. p is equal to [n−[a·a')+(b·b')+(c·c')]]. Each of $L_1$, $L_2$, and $L_3$ is independently a mono-, di-, tri- or polydentate ligand. Each of a, b, and c may represent mono, bis or tris ligand coordination. a is 1-10, b is 0-9, and c is 0-9, a' is the number of coordination sites of $L_1$. b' is the number of coordination sites of $L_2$. c' is the number of coordination sites of $L_3$. The total number of coordination sites in the phosphorescent complex $(L_1)_a(L_2)_b(L_3)_c(MX_p)_m$ is the sum of the denticity of each ligand bound to each metal complex $MX_p$ multiplied by the number of coordination sites of the ligand, i.e, (a·a')+(b·b')+(c·c'). [p+(a·a')+(b·b')+(c·c')] is equal to n.

If the phosphorescent complex contains more than one metal complex, then each metal complex $MX_n$ may have the same or different formulas. For example, the phosphorescent complex may comprise two metal complexes $MX_n$, i.e., m is 2, and each metal complex $MX_n$ is CuI, such that the complex has the formula $Cu_2I_2(L_1)_a(L_2)_b(L_3)_c$. Alternatively, the phosphorescent complex may comprise two metal complexes $MX_n$ and one metal complex $MX_n$, is CuI while the other metal complex has a different formula.

As used herein, the term "depositing over" includes depositing directly onto a substrate as well as depositing onto other layers that are themselves already deposited over the substrate. In particular, as used herein, the term "depositing over" refers to depositing one or more metal complexes having the formula $MX_n$ and one or more ligands $L_1$, $L_2$, and $L_3$ directly onto a substrate. In addition, the term "depositing over" also refers to depositing one or more metal complexes having the formula $MX_n$ and one or more ligands $L_1$, $L_2$, and $L_3$ onto another layer, e.g., an organic layer of an OLED, which is already deposited over the substrate.

Preferably, the metal complex is copper (I). More preferably, the metal complex is CuI.

At least one of the ligands $L_1$, $L_2$, and $L_3$ may be a neutral ligand. In one aspect, at least one of $L_1$, $L_2$, and $L_3$ is a neutral ligand that is coordinated to the Cu through a C, N, O, P or S atom. Preferably, at least one of $L_1$, $L_2$, and $L_3$ is a neutral ligand that is coordinated to the Cu through a N atom.

In another aspect, each of $L_1$, $L_2$, and $L_3$ is a neutral ligand that is coordinated to the Cu through a C, N, O, P or S atom. Preferably, each of $L_1$, $L_2$, and $L_3$ is a neutral ligand that is coordinated to the Cu through a N atom.

In yet another aspect, at least one of $L_1$, $L_2$, and $L_3$ is selected from the group consisting of:

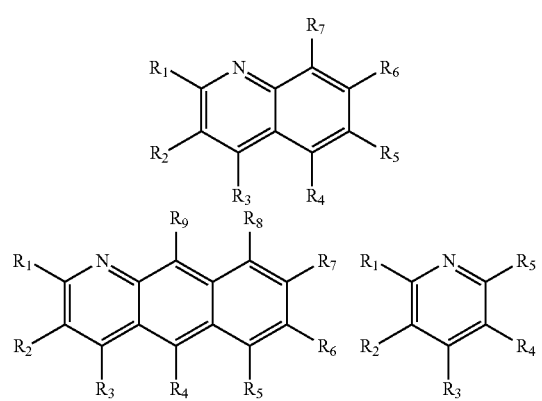

-continued

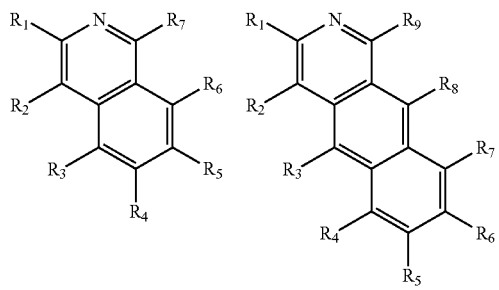

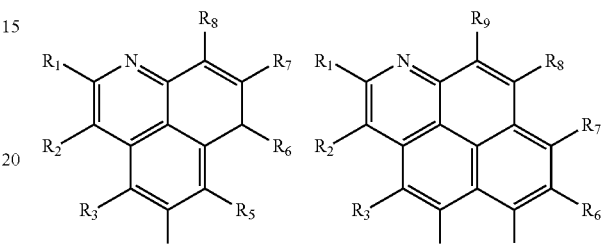

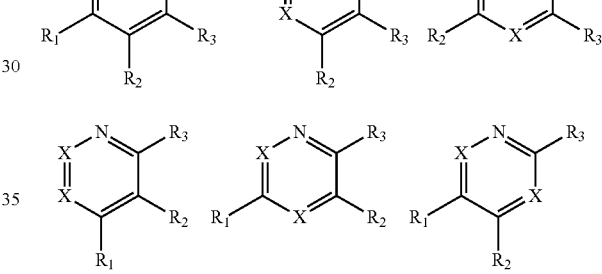

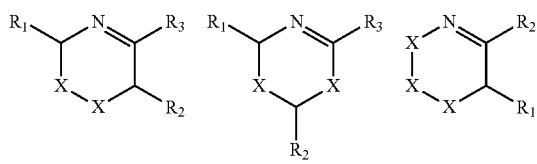

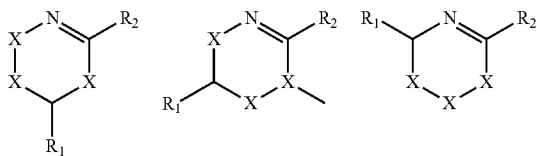

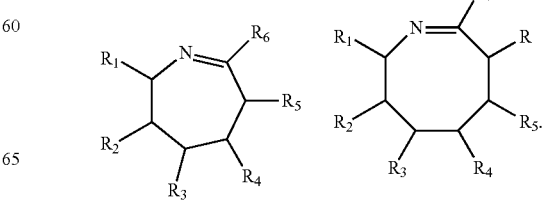

X is S, O, or NR. R, $R_1$, $R_2$, $R_3$, $R_4$, $R_5$, $R_6$, $R_7$, $R_8$ and $R_9$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfinyl, phosphino, and combinations thereof. The ligand is coordinated to the metal M via at least atom of the ligand.

Specific examples of ligands $L_1$, $L_2$, and $L_3$ are provided. In one aspect, at least one of $L_1$, $L_2$, and $L_3$ is selected from the group consisting of:

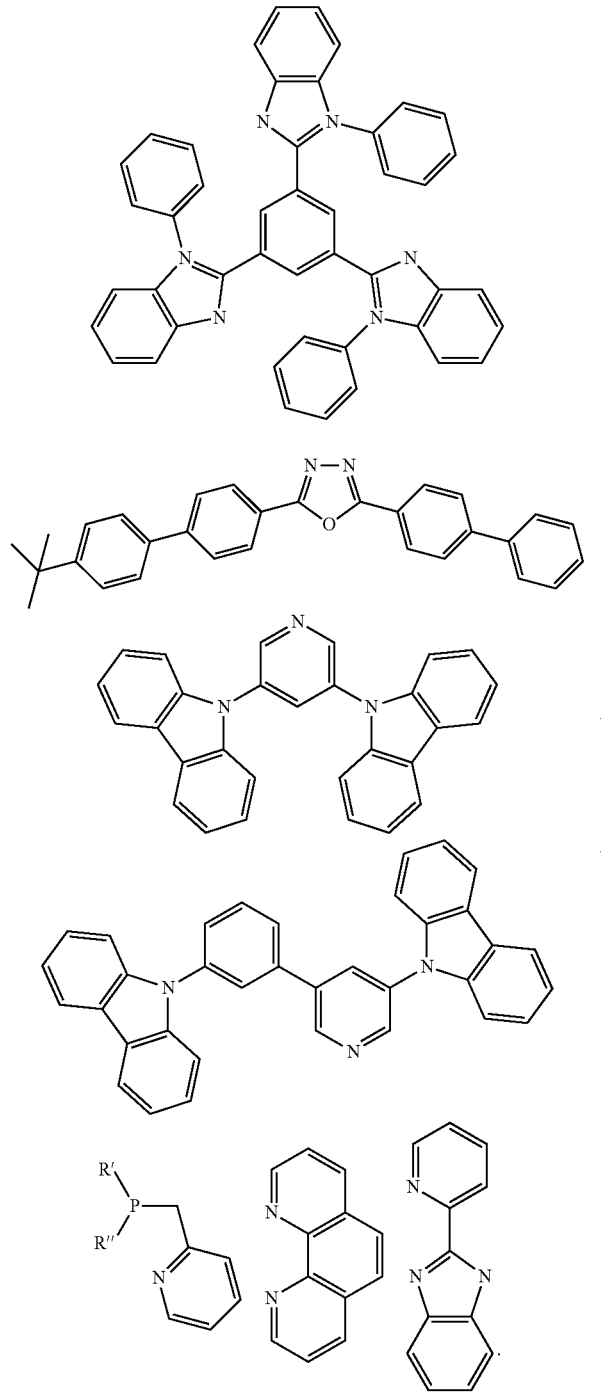

R' and R" are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

Alternatively, at least one of the ligands $L_1$, $L_2$, and $L_3$ may be a charged ligand. In one aspect, at least one of $L_1$, $L_2$, and $L_3$ is a charged ligand having the formula:

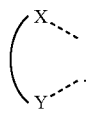

Y and Z are independently selected from the group consisting of C, N, O, P and S.

In another aspect,

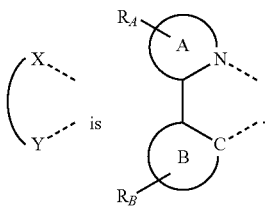

A and B are each independently a 5 or 6-membered aromatic or heteroaromatic ring. A-B represents a bonded pair of aromatic or heteroaromatic rings coordinated to the metal via a nitrogen atom on ring A and an $sp^2$ hybridized carbon atom on ring B. Each of $R_A$ and $R_B$ may represent mono, di, tri, or tetra substituents. Each of $R_A$ and $R_B$ substituents are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

The phosphorescent complex obtained from the method may be homoleptic or heteroleptic. In one aspect, b is 0 and c is 0, i.e., homoleptic. In another aspect, at least one of b and c is equal to 1, i.e., heteroleptic.

The phosphorescent complex obtained using the methods provided may or may not contain one or more halides after the metal complex has been reacted with at least one of the ligands. In one aspect, p is 0, i.e., the phosphorescent complex $(L_1)_a(L_2)_b(L_3)_c(MX_p)_m$ does not contain any halide because all of the halides present in the one or more metal complexes $MX_n$ have been removed after the metal complex was reacted with at least one of $L_1$, $L_2$ and $L_3$.

Specific examples of the phosphorescent complex obtained from the method are provided. In one aspect, the phosphorescent complex is selected from the group consisting of:

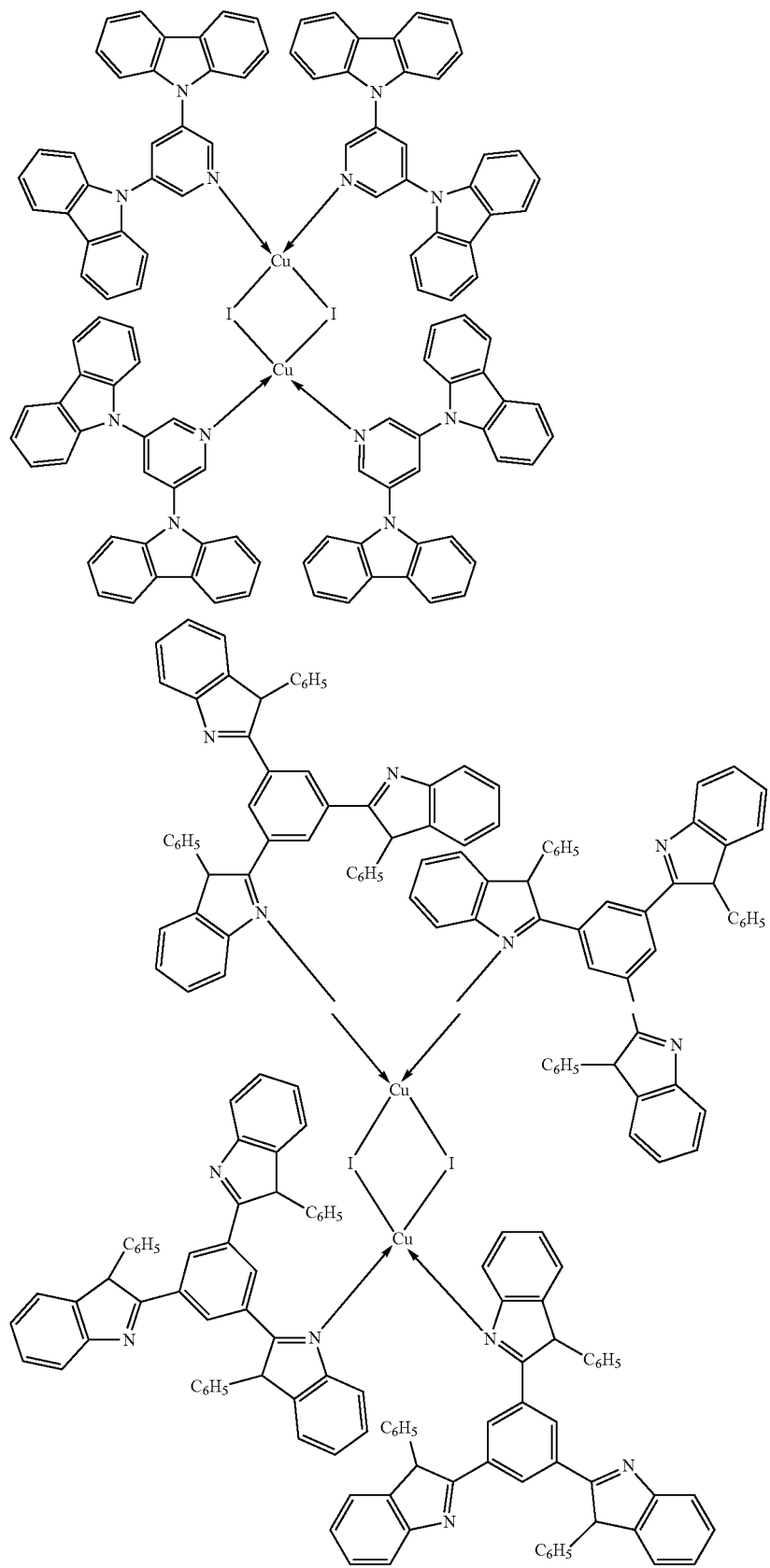

-continued

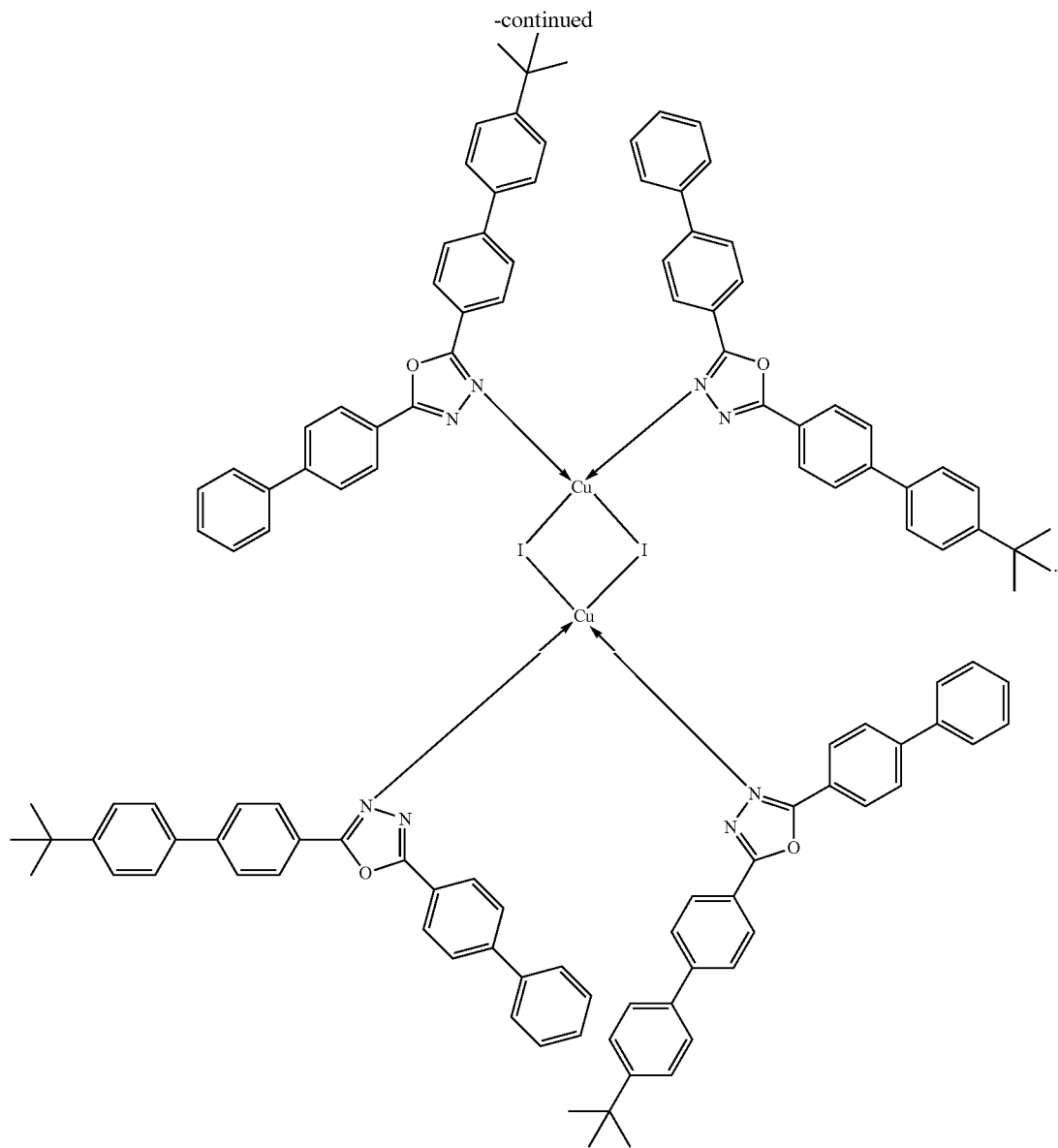

In one aspect, the one or more metal complexes having the formula $MX_n$ and the one or more ligands $L_1$, $L_2$, and $L_3$ are deposited by solution processing. In another aspect, the one or more metal complexes having the formula $MX_n$ and the one or more ligands $L_1$, $L_2$, and $L_3$ are deposited by thermal evaporation.

In one aspect, the one or more metal complexes $MX_n$ is mixed with an organic solvent to form a first solution and at least one of $L_1$, $L_2$, and $L_3$ is mixed with an organic solvent to form a second solution, prior to depositing over the substrate, and then the first solution and the second solution are deposited in combination over the substrate.

In another aspect, the method further comprises providing a first electrode disposed over the substrate, depositing the one or more metal complexes having the formula $MX_n$ and the ligand L on the first electrode, and depositing a second electrode. Preferably, the first electrode is an anode and the second electrode is a cathode.

In another aspect, the method further comprises providing a first electrode disposed over the substrate, providing an organic layer disposed over the first electrode, depositing the one or more metal complexes having the formula $MX_n$ and the ligand L on the first electrode, and depositing a second electrode. Preferably, the first electrode is an anode and the second electrode is a cathode.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal phosphorescent complex, and a cross-linkable compounds.

Examples of aromatic amine derivatives used in HIL or HTL include, but not limit to the following general structures:

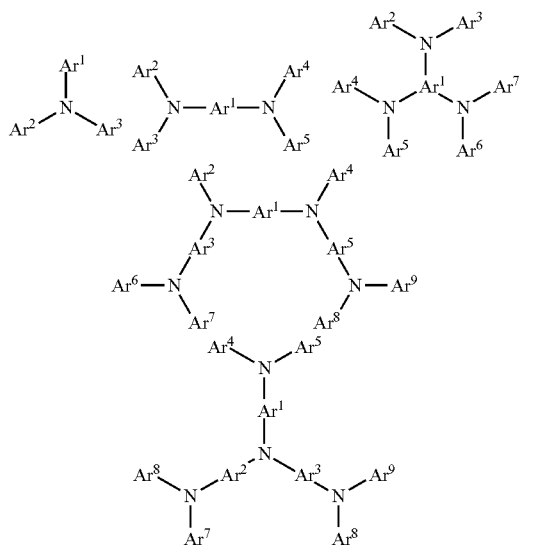

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

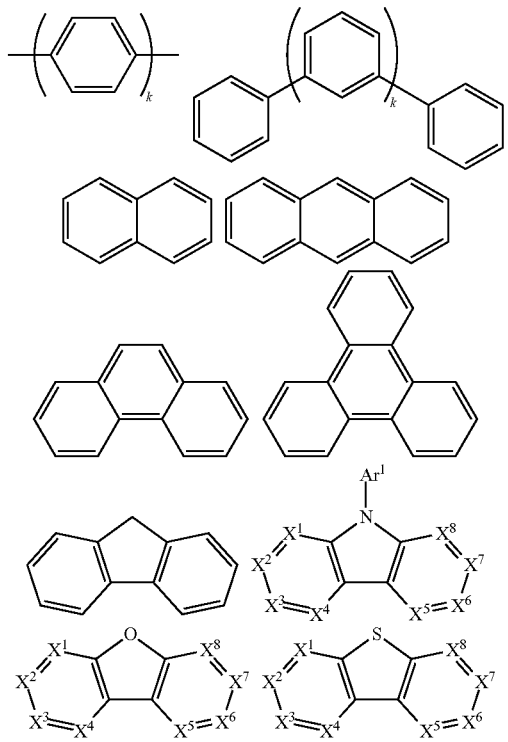

k is an integer from 1 to 20; $X^1$ to $X^8$ is C (including CH) or N; $Ar^1$ has the same group defined above.

Examples of metal phosphorescent complexes used in HIL or HTL include, but not limit to the following general formula:

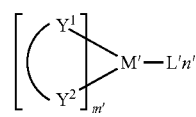

M' is a metal, having an atomic weight greater than 40; ($Y^1$—$Y^2$) is a bidentate ligand, $Y^1$ and $Y^2$ are independently selected from C, N, O, P, and S; L' is an ancillary ligand; m is an integer value from 1 to the maximum number of ligands that may be attached to the metal; and m'+n' is the maximum number of ligands that may be attached to the metal.

In one aspect, ($Y^1$—$Y^2$) is a 2-phenylpyridine derivative.

In another aspect, ($Y^1$—$Y^2$) is a carbene ligand.

In another aspect, M' is selected from Ir, Pt, Os, and Zn.

In a further aspect, the metal phosphorescent complex has a smallest oxidation potential in solution vs. Fc$^+$/Fc couple less than about 0.6 V.

Host:

The light emitting layer of the organic EL device of the present invention preferably contains at least a metal phosphorescent complex as light emitting material, and may contain a host material using the metal phosphorescent complex as a dopant material. Examples of the host material are not particularly limited, and any metal phosphorescent complexes or organic compounds may be used as long as the triplet energy of the host is larger than that of the dopant.

Examples of metal phosphorescent complexes used as host are preferred to have the following general formula:

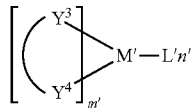

M' is a metal; $(Y^3-Y^4)$ is a bidentate ligand, $Y^3$ and $Y^4$ are independently selected from C, N, O, P, and S; L' is an ancillary ligand; m is an integer value from 1 to the maximum number of ligands that may be attached to the metal; and m'+n' is the maximum number of ligands that may be attached to the metal.

In one aspect, the metal phosphorescent complexes are:

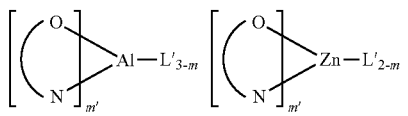

(O—N) is a bidentate ligand, having metal coordinated to atoms O and N.

In another aspect, M' is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxadiazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

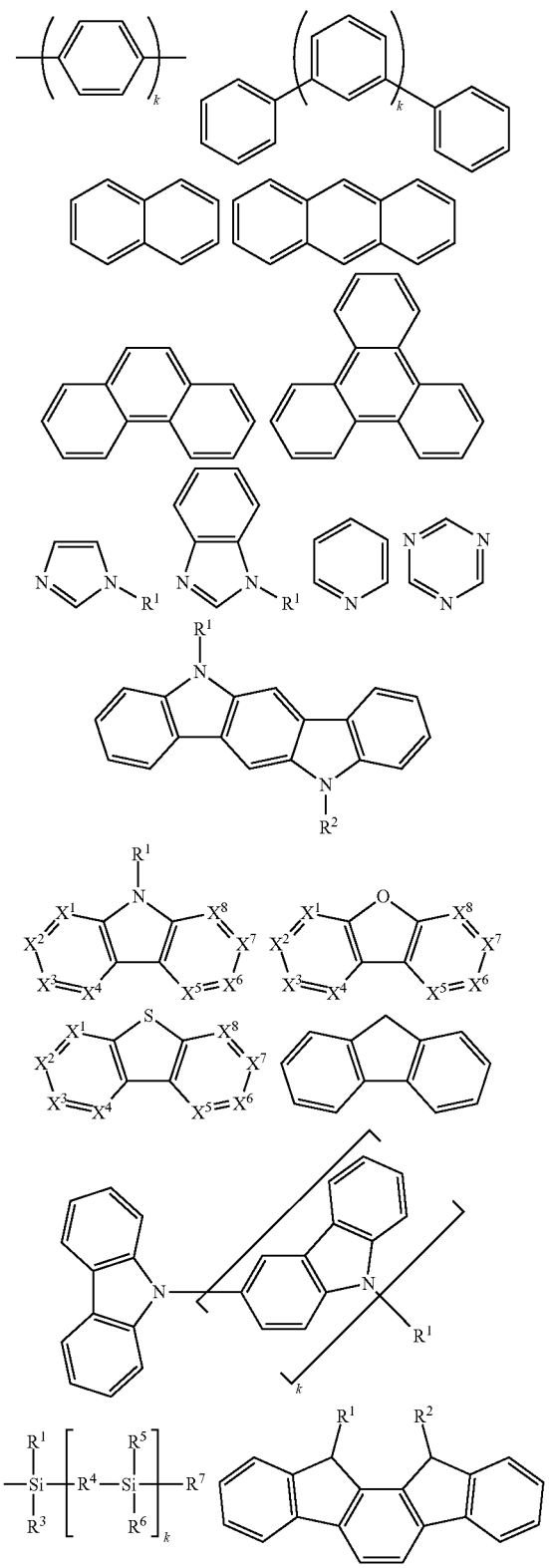

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

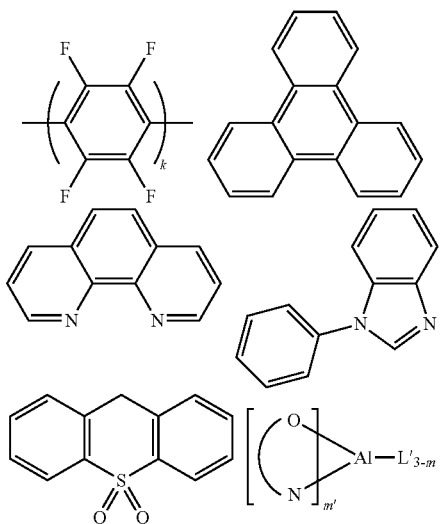

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal phosphorescent complexes or organic compounds may be used as long as they are typically used to transport electrons.

In one aspect, compound used in ETL contains at least one of the following groups in the molecule:

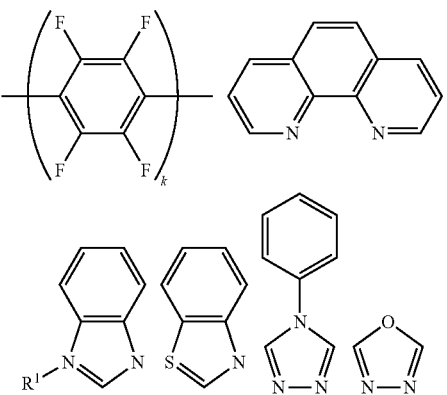

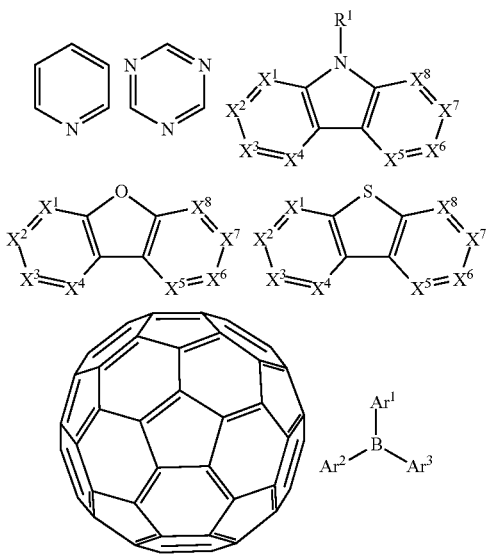

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal phosphorescent complexes used in ETL contains, but not limit to the following general formula:

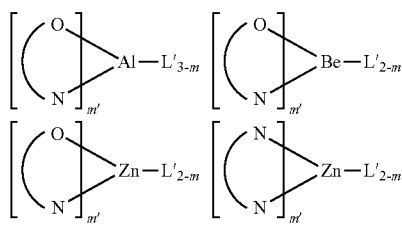

(O—N) or (N—N) is a bidentate ligand, having metal coordinated to atoms O, N or N, N; L' is an ancillary ligand; m' is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphryin compounds | *[copper phthalocyanine structure]* | Appl. Phys. Lett. 69, 2160 (1996) |
| Starburst triarylamines | *[starburst triarylamine structure]* | J. Lumin. 72-74, 985 (1997) |
| CF$_x$ Fluorohydrocarbon polymer | $-\!\!+\!\text{CH}_x\text{F}_y\!+\!\!-$ | Appl. Phys. Lett. 78, 673 (2001) |
| Conducting polymers (e.g., PEDOT:PSS, polyaniline, polypthiophene) | *[PEDOT:PSS structure with SO$_3^-$(H$^+$)]* | Synth. Met. 87, 171 (1997) WO2007002683 |
| Phosphonic acid and sliane SAMs | $\left( N\!-\!\!\left\langle\phantom{x}\right\rangle\!\!-\!\text{SiCl}_3 \right)_3$ | US20030162053 |

TABLE 1-continued
| MATERIAL | EXAMPLES OF MATERIAL | PUBLICATIONS |
|---|---|---|
| Triarylamine or polythiophene polymers with conductivity dopants | 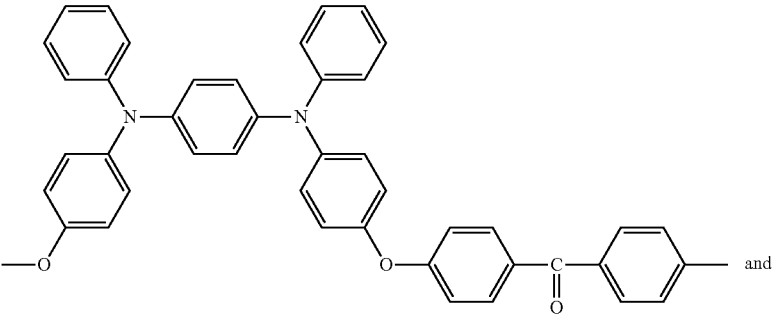 and 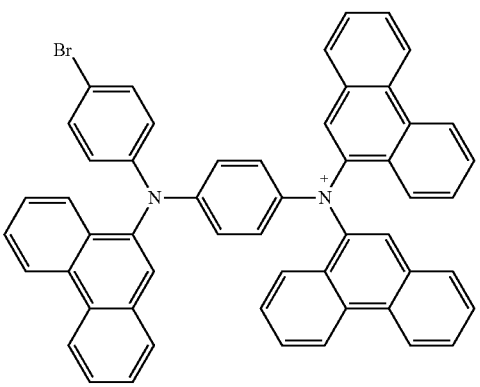 [SMILES: Brc1ccc(N(c2ccc(N(c3cc4ccccc4c4ccccc34)c3cc4ccccc4c4ccccc34)cc2)c2cc3ccccc3c3ccccc23)cc1] 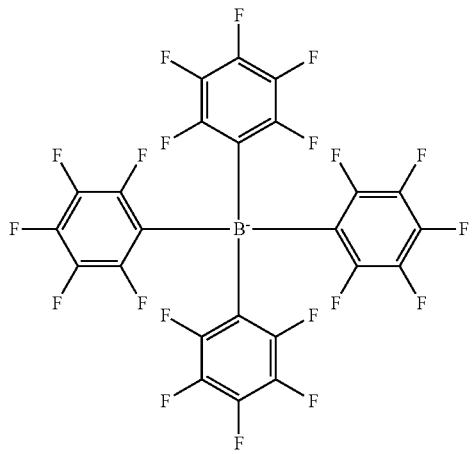 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Arylamines phosphorescent complexed with metal oxides such as molybdenum and tungsten oxides | 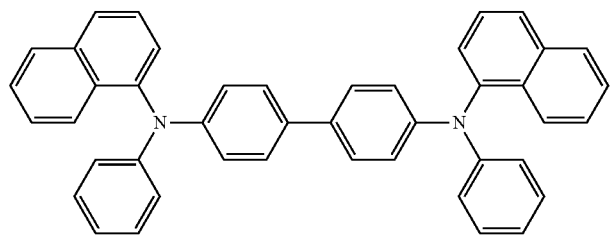 [SMILES: c1ccc(N(c2ccc(-c3ccc(N(c4ccccc4)c4cccc5ccccc45)cc3)cc2)c2cccc3ccccc23)cc1] +MoO$_x$ | SID Symposium Digest, 37, 923 (2006) WO2009018009 |

TABLE 1-continued

| MATERIAL | EXAMPLES OF MATERIAL | PUBLICATIONS |
|---|---|---|
| p-type semiconducting organic phosphorescent complexes | | US20020158242 |
| Metal organometallic phosphorescent complexes | | US20060240279 |
| Cross-linkable compounds | | US20080220265 |

Hole transporting materials

| | | |
|---|---|---|
| Triarylamines (e.g., TPD, α-NPD) | | Appl. Phys. Lett. 51, 913 (1987) |
| | | US5061569 |

TABLE 1-continued
| MATERIAL | EXAMPLES OF MATERIAL | PUBLICATIONS |
|---|---|---|
| | 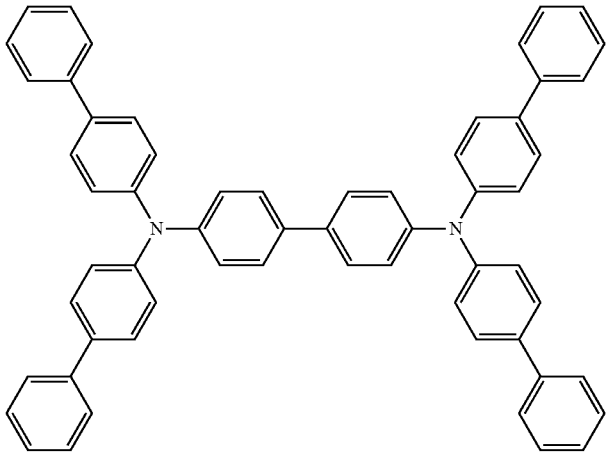 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 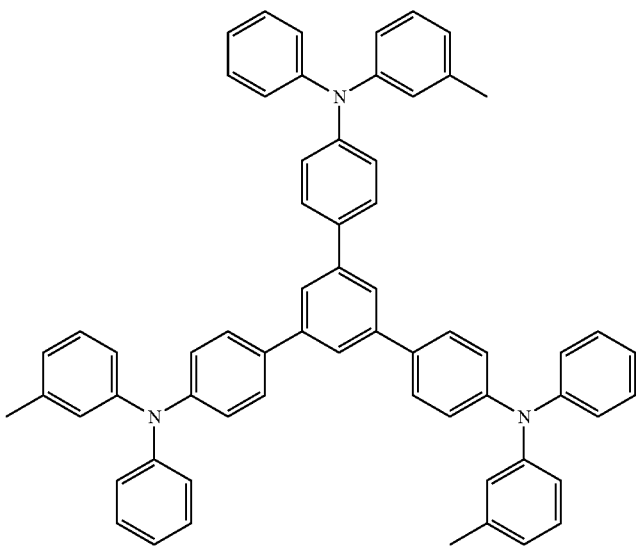 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 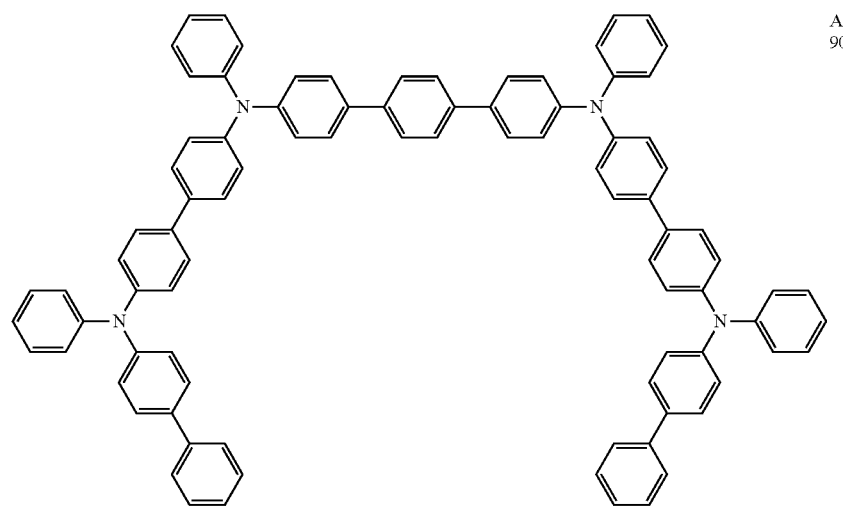 | Appl. Phys. Lett. 90, 183503 (2007) |

TABLE 1-continued
| MATERIAL | EXAMPLES OF MATERIAL | PUBLICATIONS |
|---|---|---|
| | 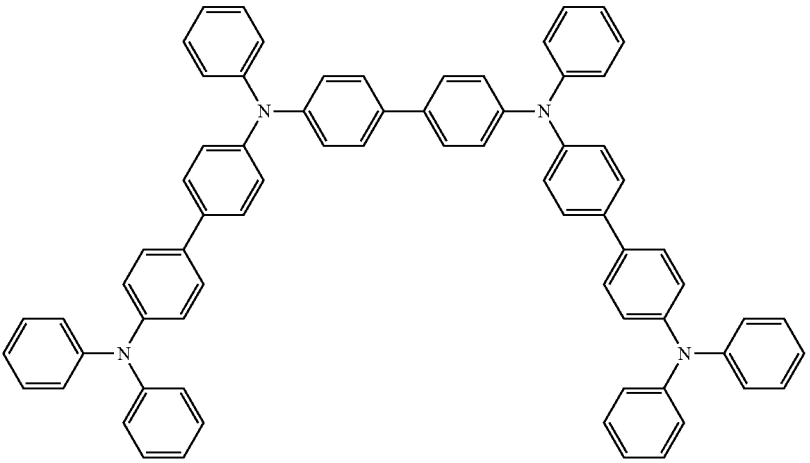 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 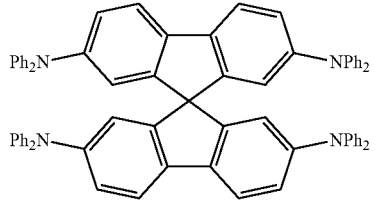 | Synth. Met. 91, 209 (1997) |
| Arylamine carbazole compounds | 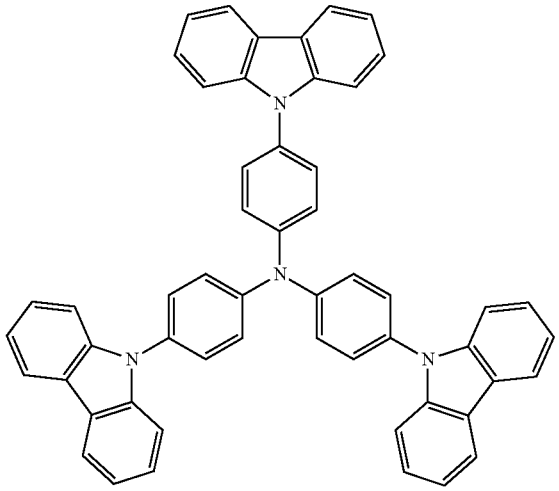 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzo-thiophene/ (di)benzofuran | 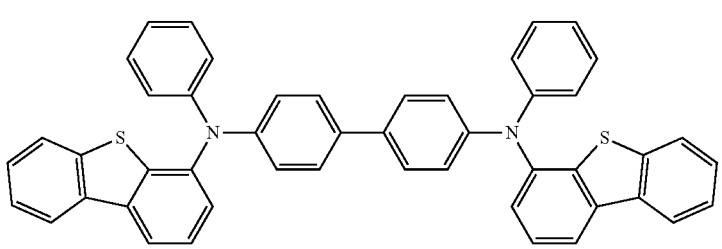 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |

TABLE 1-continued
| MATERIAL | EXAMPLES OF MATERIAL | PUBLICATIONS |
|---|---|---|
| Indolocarbazoles | 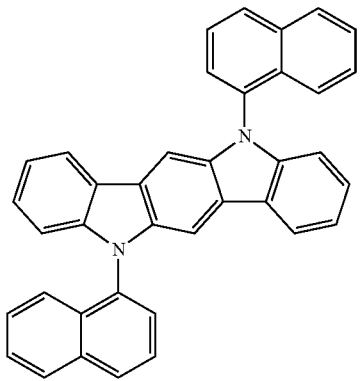 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 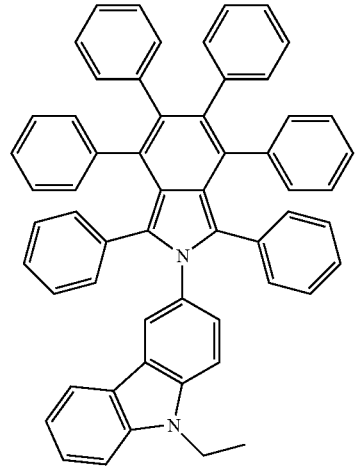 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene phosphorescent complexes | 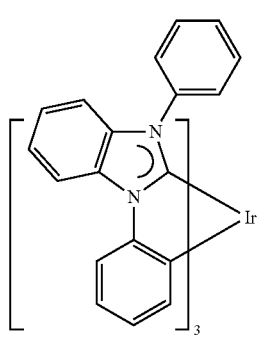 | US20080018221 |
Phosphorescent OLED host materials
Red hosts
| Arylcarbazoles | 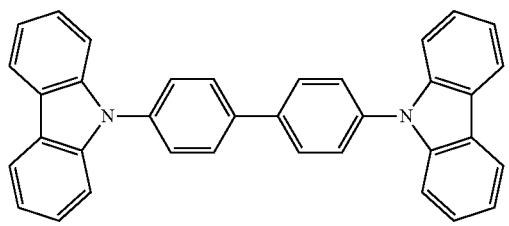 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 1-continued
| MATERIAL | EXAMPLES OF MATERIAL | PUBLICATIONS |
|---|---|---|
| Metal 8-hydroxy-quinolates (e.g., Alq$_3$, BAlq) | 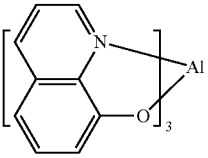 | Nature 395, 151 (1998) |
| | 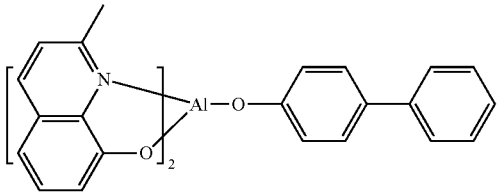 | US20060202194 |
| | 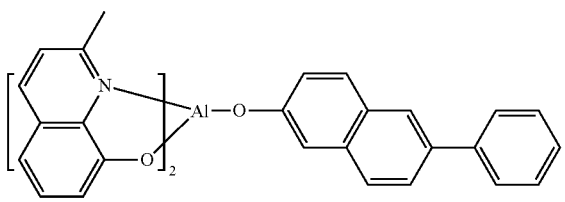 | WO2005014551 |
| | 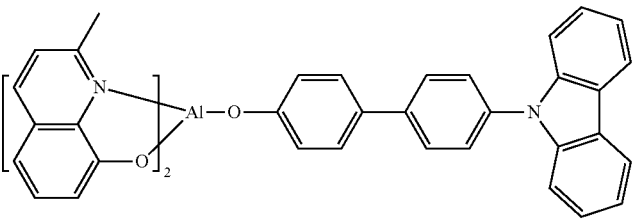 | WO2006072002 |
| Metal phenoxy-benzothiazole compounds | 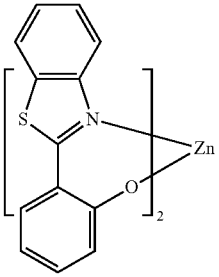 | Appl. Phys. Lett. 90, 123509 (2007) |
| Conjugated oligomers and polymers (e.g., polyfluorene) | 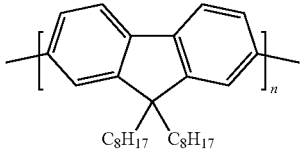 | Org. Electron. 1, 15 (2000) |
| Aromatic fused rings | 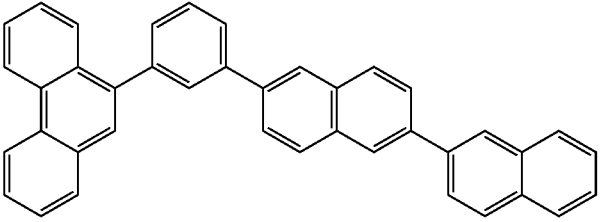 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 1-continued

| MATERIAL | EXAMPLES OF MATERIAL | PUBLICATIONS |
|---|---|---|
| Zinc phosphorescent complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 1-continued

| MATERIAL | EXAMPLES OF MATERIAL | PUBLICATIONS |
|---|---|---|
|  |  | US20060280965 |
|  |  | WO2009021126 |
| Donor acceptor type molecules |  | WO2008056746 |
| Aza-carbazole/ DBT/DBF |  | JP2008074939 |
| Polymers (e.g., PVK) |  | Appl. Phys. Lett. 77, 2280 (2000) |

TABLE 1-continued

| MATERIAL | EXAMPLES OF MATERIAL | PUBLICATIONS |
| --- | --- | --- |
| Spirofluorene compounds | | WO2004093207 |
| Metal phenoxy-benzooxazole compounds | | WO2005089025 |
| | | WO2006132173 |
| | | JP200511610 |
| Spirofluorene-carbazole compounds | | JP2007254297 |

TABLE 1-continued
| MATERIAL | EXAMPLES OF MATERIAL | PUBLICATIONS |
|---|---|---|
| | 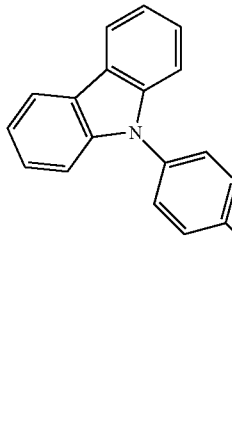 | JP2007254297 |
| Indolocabazoles | 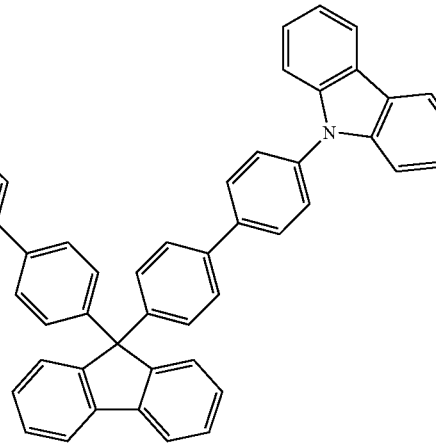 | WO2007063796 |
| | 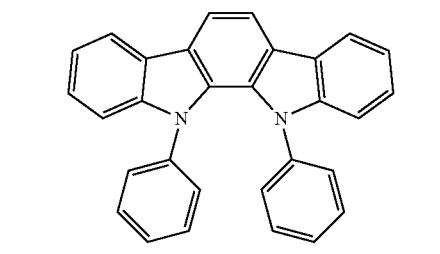 [SMILES: c1ccc(-n2c3ccccc3c3ccc4c5ccccc5n(-c5ccccc5)c4c32)cc1] | WO2007063754 |
| 5-member ring electron deficient heterocycles (e.g., triazole, oxadiazole) | 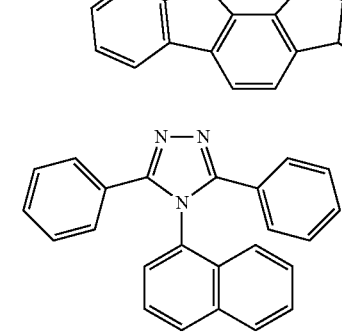 | J. Appl. Phys. 90, 5048 (2001) |
| | 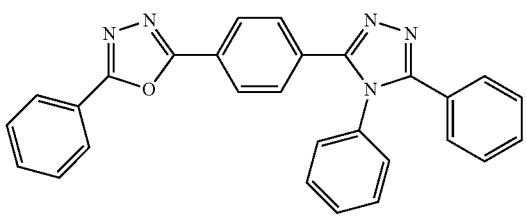 [SMILES: c1ccc(-c2nnc(-c3ccc(-c4nnc(-c5ccccc5)n4-c4ccccc4)cc3)o2)cc1] | WO2004107822 |

TABLE 1-continued

| MATERIAL | EXAMPLES OF MATERIAL | PUBLICATIONS |
| --- | --- | --- |
| Tetraphenylene phosphorescent complexes | | US20050112407 |
| Metal phenoxypyridine compounds | | WO2005030900 |
| Metal coordination phosphorescent complexes (e.g., Zn, Al with N N ligands) | | US20040137268, US20040137267 |
| Blue hosts | | |
| Arylcarbazoles | | Appl. Phys. Lett, 82, 2422 (2003) |
| | | US20070190359 |

TABLE 1-continued
| MATERIAL | EXAMPLES OF MATERIAL | PUBLICATIONS |
|---|---|---|
| Dibenzothiophene/ Dibenzofuran- carbazole compounds | 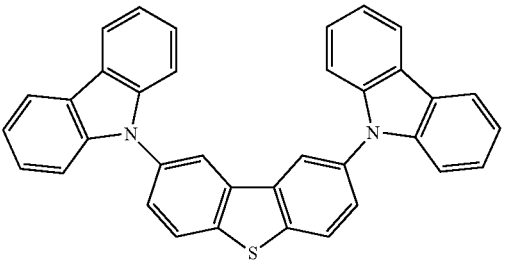 [SMILES: c1ccc2c(c1)c1ccccc1n2-c1ccc2sc3ccc(-n4c5ccccc5c5ccccc54)cc3c2c1] | WO2006114966, US20090167162 |
| | 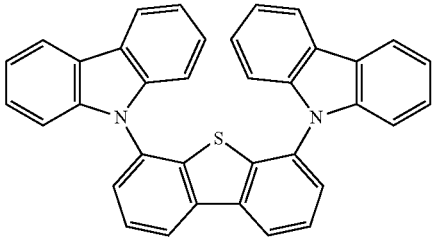 [SMILES: c1cc(-n2c3ccccc3c3ccccc32)c2sc3c(-n4c5ccccc5c5ccccc54)cccc3c2c1] | US20090167162 |
| | 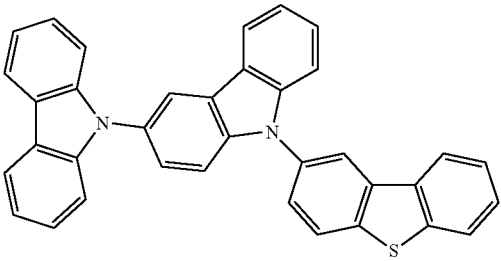 [SMILES: c1ccc2c(c1)sc1ccc(-n3c4ccccc4c4cc(-n5c6ccccc6c6ccccc65)ccc43)cc12] | WO2009086028 |
| | 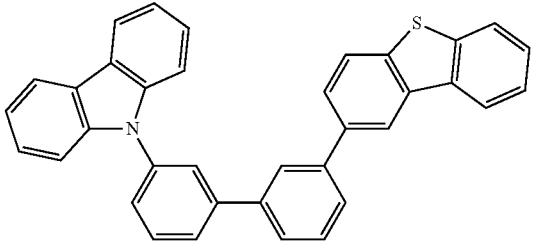 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 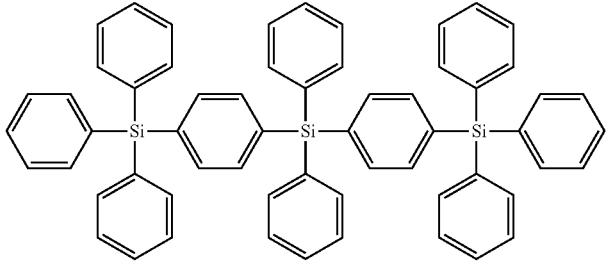 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 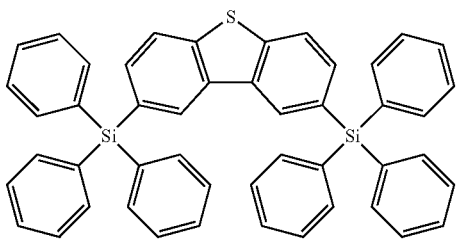 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 1-continued

| MATERIAL | EXAMPLES OF MATERIAL | PUBLICATIONS |
| --- | --- | --- |
| Silicon/ Germanium aryl compounds | | EP2034538A |
| Aryl benzoyl ester | | WO2006100298 |
| High triplet metal organometallic phosphorescent complex | | US7154114 |
| Phosphorescent dopants | | |
| Red dopants | | |
| Heavy metal porphyrins (e.g., PtOEP) | | Nature 395, 151 (1998) |
| Iridium (III) organometallic phosphorescent complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 1-continued
| MATERIAL | EXAMPLES OF MATERIAL | PUBLICATIONS |
|---|---|---|
| | 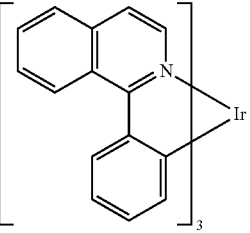 | US20070087321 |
| | 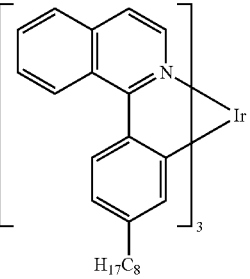 | Adv. Mater. 19, 739 (2007) |
| | 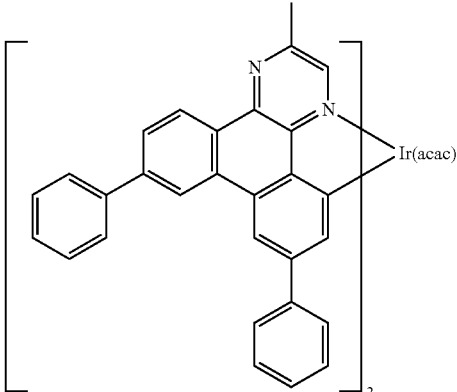 | WO2009100991 |
| | 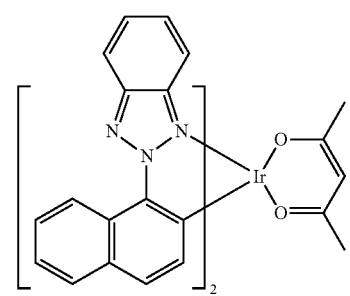 | WO2008101842 |
| Platinum (II) organometallic phosphorescent complexes | 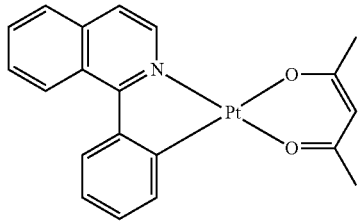 | WO2003040257 |

TABLE 1-continued
| MATERIAL | EXAMPLES OF MATERIAL | PUBLICATIONS |
| --- | --- | --- |
| Osminum (III) phosphorescent complexes | 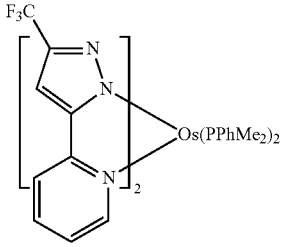 | Chem. Mater. 17, 3532 (2005) |
| Ruthenium (II) phosphorescent complexes | 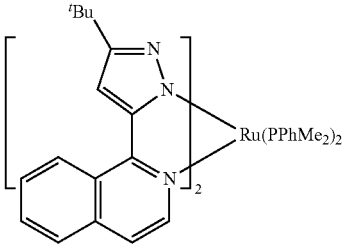 | Adv. Mater. 17, 1059 (2005) |
| Rhenium (I), (II), and (III) phosphorescent complexes | 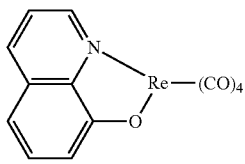 | US20050244673 |
| Green dopants | | |
| Iridium (III) organometallic phosphorescent complexes | 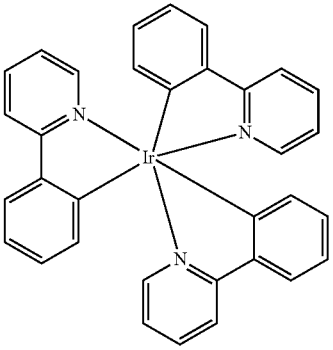<br>and its derivatives<br>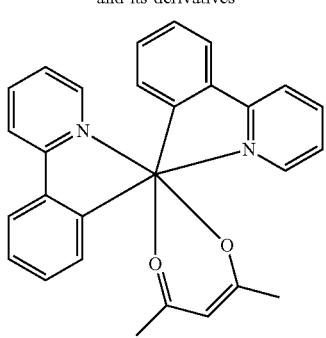 | Inorg. Chem. 40, 1704 (2001)<br><br>US20020034656 |

TABLE 1-continued

| MATERIAL | EXAMPLES OF MATERIAL | PUBLICATIONS |
|---|---|---|
| | | US7332232 |
| | | US20090108737 |
| | | US20090039776 |
| | | US6921915 |

TABLE 1-continued

| MATERIAL | EXAMPLES OF MATERIAL | PUBLICATIONS |
|---|---|---|
| | (structure) | US6687266 |
| | (structure) | Chem. Mater. 16, 2480 (2004) |
| | (structure) | US20070190359 |
| | (structure) | US20060008670<br>JP2007123392 |
| | (structure) | Adv. Mater. 16, 2003 (2004) |

TABLE 1-continued
| MATERIAL | EXAMPLES OF MATERIAL | PUBLICATIONS |
|---|---|---|
| | 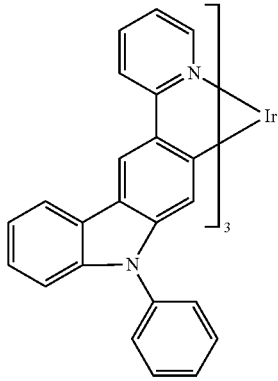 | Angew. Chem. Int. Ed. 2006, 45, 7800 |
| | 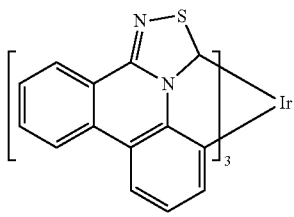 | WO2009050290 |
| | 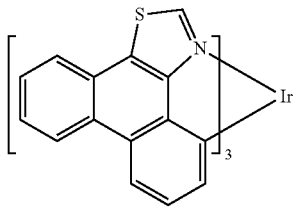 | US20090165846 |
| | 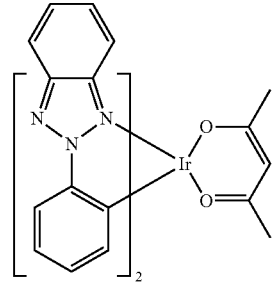 | US20080015355 |
| Monomer for polymeric metal organometallic compounds | 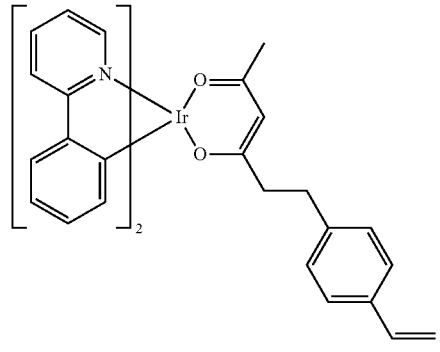 | US7250226, US7396598 |

TABLE 1-continued
| MATERIAL | EXAMPLES OF MATERIAL | PUBLICATIONS |
|---|---|---|
| Pt (II) organometallic phosphorescent complexes, including polydentated ligands | 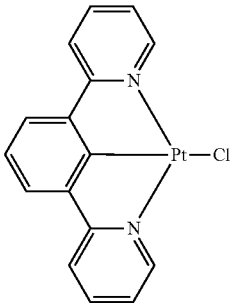 | Appl. Phys. Lett. 86, 153505 (2005) |
| | 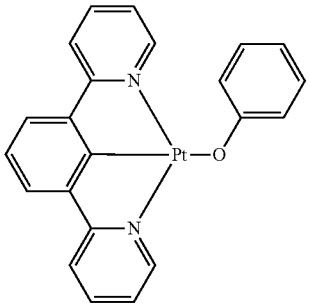 | Appl. Phys. Lett. 86, 153505 (2005) |
| | 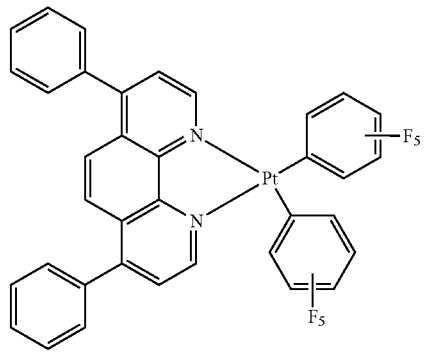 | Chem. Lett. 34, 592 (2005) |
| | 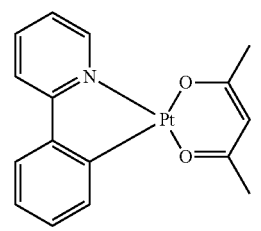 | WO2002015645 |
| | 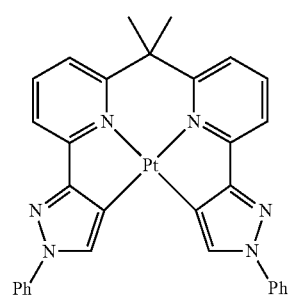 | US20060263635 |

TABLE 1-continued

| MATERIAL | EXAMPLES OF MATERIAL | PUBLICATIONS |
|---|---|---|
| Cu phosphorescent complexes | | WO200900673 |
| Gold phosphorescent complexes | | Chem. Commun. 2906 (2005) |
| Rhenium (III) phosphorescent complexes | | Inorg. Chem. 42, 1248 (2003) |
| Deuterated organometallic phosphorescent complexes | | US20030138657 |

TABLE 1-continued

| MATERIAL | EXAMPLES OF MATERIAL | PUBLICATIONS |
|---|---|---|
| Organometallic phosphorescent complexes with two or more metal centers | | US20030152802 |
| | | US7090928 |
| Blue dopants | | |
| Iridium (III) organometallic phosphorescent complexes | | WO2002002714 |
| | | WO2006009024 |
| | | US20060251923 |

TABLE 1-continued

| MATERIAL | EXAMPLES OF MATERIAL | PUBLICATIONS |
|---|---|---|
| | | US7393599, WO2006056418, US20050260441, WO2005019373 |
| | | US7534505 |
| | | US7445855 |
| | | US20070190359, US20080297033 |
| | | US7338722 |
| | | US20020134984 |

| MATERIAL | EXAMPLES OF MATERIAL | PUBLICATIONS |
|---|---|---|
| | 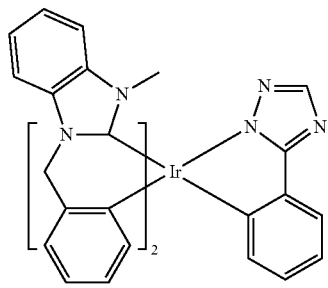 | Angew. Chem. Int. Ed. 47, 1 (2008) |
| | 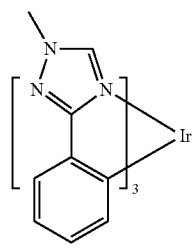 | Chem. Mater. 18, 5119 (2006) |
| | 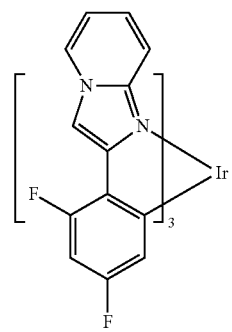 | Inorg. Chem. 46, 4308 (2007) |
| | 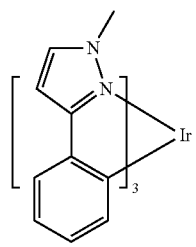 | WO2005123873 |
| | 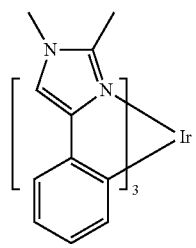 | WO2005123873 |
| | 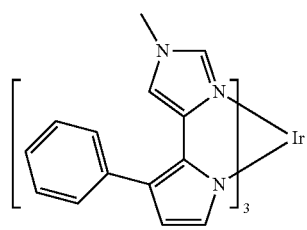 | WO2007004380 |

TABLE 1-continued

| MATERIAL | EXAMPLES OF MATERIAL | PUBLICATIONS |
|---|---|---|
| | [Ir complex structure] | WO2006082742 |
| Osmium (II) phosphorescent complexes | [Os complex with benzimidazole ligands] | US7279704 |
| | [Os(PPh₃) complex with pyrazole-pyridine ligand] | Organometallics 23, 3745 (2004) |
| Gold phosphorescent complexes | [Ph₂P-CH₂-PPh₂ bridged Au-Cl dimer] | Appl. Phys. Lett. 74, 1361 (1999) |

TABLE 1-continued

| MATERIAL | EXAMPLES OF MATERIAL | PUBLICATIONS |
| --- | --- | --- |
| Platinum (II) phosphorescent complexes | | WO2006098120, WO2006103874 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxy-quinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 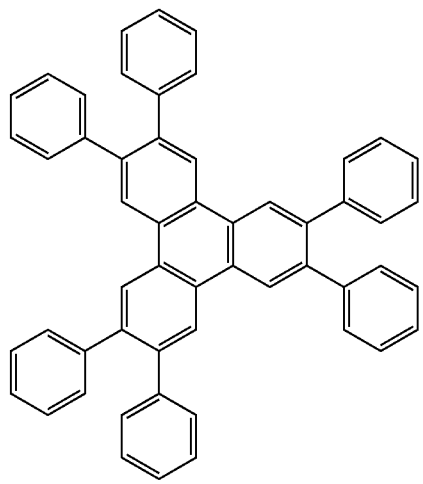 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 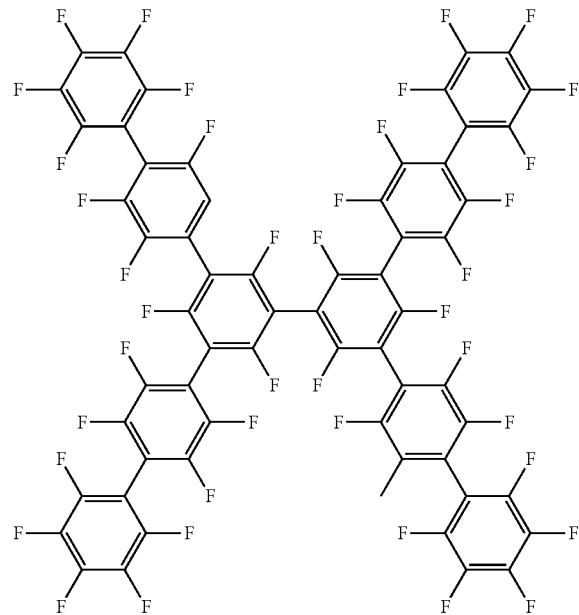 [SMILES: Cc1c(F)c(-c2c(F)c(-c3c(F)c(F)c(-c4c(F)c(F)c(F)c(F)c4F)c(F)c3F)c(F)c(-c3c(F)c(-c4cc(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 1-continued

| MATERIAL | EXAMPLES OF MATERIAL | PUBLICATIONS |
|---|---|---|
| Phenothiazine-S-oxide | | WO2008132085 |
| Electron transporting materials | | |
| Anthracene-benzoimidazole compounds | | WO2003060956 |
| | | US20090179554 |
| Aza triphenylene derivatives | | US20090115316 |

TABLE 1-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxy-quinolates (e.g., $Alq_3$, $Zrq_4$) | | Appl. Phys. Lett. 51, 913 (1987) US7230107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 1-continued

| MATERIAL | EXAMPLES OF MATERIAL | PUBLICATIONS |
|---|---|---|
| | | Appl. Phys. Lett. 55, 1489 (1989) |
| | | Jpn. J. Apply. Phys. 32, L917 (1993) |
| Silole compounds | | Org. Electron. 4, 133 (2003) |
| Arylborane compounds | | J. Am. Chem. Soc. 120, 9714 (199) |
| Fluorinated aromatic compounds | | J. Am. Chem. Soc. 122, 1832 (2000) |
| Fullerene (e.g., C60) | | US20090101870 |

TABLE 1-continued

| MATERIAL | EXAMPLES OF MATERIAL | PUBLICATIONS |
|---|---|---|
| Triazine phosphorescent complexes | | US20040036077 |
| Zn (N^N) phosphorescent complexes | | US6528187 |

EXPERIMENTAL

Three organic molecules (TPBi, PBD, and mCPy) were used to demonstrate the methods provided. In particular, the photophysical properties of the co-deposited film and the performance of an OLEDs comprising the film were studied. Additionally, luminescent species in the co-deposited CuI:mCPy film were studied.

Example 1

Co-Deposition of CuI and TPBi for OLEDs

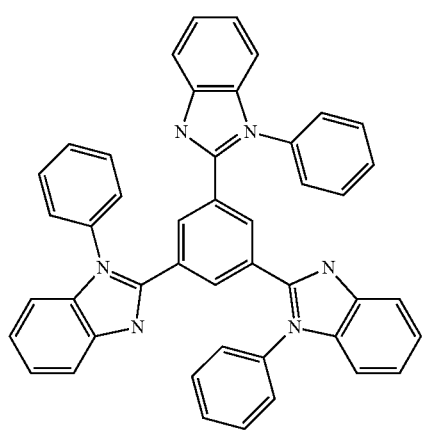

A series of CuI:TPBi films with different molar ratios were made by spin coating at room temperature. Table 2 provides the PLQY and lifetime data of spin cast CuI:TPBi films with different ratios. In details, 19.1 mg (0.1 mmol) CuI was dissolved in 5 mL $CH_3CN$, 65.5 mg (0.1 mmol) TPBi was dissolved in 25 mL $CH_3CN$. Films were then obtained by spin coating mixed solutions with different amount of CuI and TPBi, i.e. mixture of 200 μL CuI solution and 1000 μL TPBi solution was used to make 1:1 film. The photoluminescent spectra, lifetime, and photoluminescence quantum yield (PLQY) were examined under $N_2$.

TABLE 2

| CuI:TPBi (molar ratio) | PLQY (%) | Lifetime (lls) |
|---|---|---|
| 1:1 | 2.1 | 0.78 |
| 1:2 | 10.6 | 1.87 |
| 1:3 | 12.7 | 2.30 |
| 1:4 | 16.3 | 2.66 |
| 1:5 | 16.4 | 2.53 |
| 1:7 | 16.6 | 2.68 |
| 1:10 | 16.8 | 2.66 |

FIG. 3 shows photoluminescent spectra of CuI:TPBi (molar ratio 1:4) film and neat TPBi film. The CuI:TPBi film has two emission peaks, with CuI:TPBi ratio varied from 1:1 to 1:10. One emission around 390 nm is likely due to TPBi, which consist with the emission of neat TPBi film. The other emission around 550 nm with decay lifetime of several microseconds is assigned to CuI:TPBi complex. By varying the molar ratio, it is found that the CuI:TPBi film shows maximum PLQY around 17% (Table 2).

Since CuI can react with TPBi to form luminescent film easily, a device ITO/NPD (1000 Å)/CuI:TPBi (1:1.7, 100 Å)/TPBi (500 Å)/LiF (10 Å)/Al (1000 Å) was fabricated. The device was fabricated under standard OLEDs process, except the CuI:TPBi layer was made by co-depositing CuI and TPBi in vacuum chamber from different heating resources. Maximum external quantum efficiency (EQE) around 0.5% (FIG. 4) was examined in this device. As shown in FIG. 5, the device shows electroluminescence around 560 nm, which is originated from CuI:TPBi complex based on the photoluminescent study of CuI:TPBi nm mentioned above. Though there is emission around 430 nm that may due to TPBi, the device fabricated here demonstrate that the co-deposited CuI:TPBi layer can be used as emission layer in OLEDs.

Example 2

Co-Deposition of CuI and PBD for OLEDs

Similar to the CuI:TPBi system, a series of CuI:PBD films with different molar ratio were made by spin coating at room temperature prior to OLEDs fabrication. The photoluminescent spectra, lifetime, and PLQYs of these films were examined, and the data is provided in Table 3.

TABLE 3

| CuI:TPBi (molar ratio) | PLQY (%) | Lifetime (lls) |
| --- | --- | --- |
| 2:1 | 2.5 | 1.12, 0.31 |
| 1:1 | 7.2 | 1.56, 0.63 |
| 1:2 | 13.9 | 2.33 |
| 1:3 | 14.1 | 2.31 |
| 1:4 | 14.3 | 2.97 |
| 1:5 | 14.3 | 3.62 |
| 1:7 | 12.2 | 4.07 |
| 1:10 | 12.6 | 4.42 |

The CuI:PBD film has also two emission peaks with different CuI:PBD ratio, one peak around 390 nm originates from PBD and another peak around 570 nm with decay lifetime of several microseconds that from CuI:PBD complex. By varying the molar ratio of CuI and PBD, it is found that the CuI:PBD film shows maximum PLQY around 14% (Table 3). To apply CuI:PBD complex in OLEDs, a device ITO/NPD (1000 Å)/CuI:PBD (1:1, 100 Å)/PBD (500 Å)/LiF (10 Å)/Al (1000 Å) was fabricated, where the CuI:PBD layer was made by co-depositing CuI and PBD in vacuum chamber from different heating resources. The device shows maximum external quantum efficiency around 1.2% at low luminance (around 0.1 cd/m2) (FIG. 7). As shown in FIG. 8, the device has pure CuI:PBD complex emission at very low luminance, while show also emission that may from PBD at higher luminance around 430 nm. Though the electroluminescence is not pure, the device shows mainly emission from CuI:PBD complex, demonstrated that co-deposited CuI: PBD layer can be used as emission layer in OLEDs.

Example 3

Co-Deposition of CuI and mCPy for OLEDs

As shown above, both TPBi and PBD can be used to co-deposit with CuI to form luminescent film as emission layer in OLEDs. However, the CuI:TPBi and CuI:PBD films have moderate PLQYs (17% and 14%) and impure electroluminescence. To improve OLEDs performance, it is critical to explore ligand that can coordinate to CuI and form highly efficient luminescent film. It is well known that copper iodide and pyridine based complexes are highly emissive at room temperature. [Ford, P. C.; Carlati, E.; Bourassa, J., *Chemical Reviews* 1999, 99, (12), 3625.3647.] Herein, mCPy was designed to co-deposit with CuI to explore efficient OLEDs.

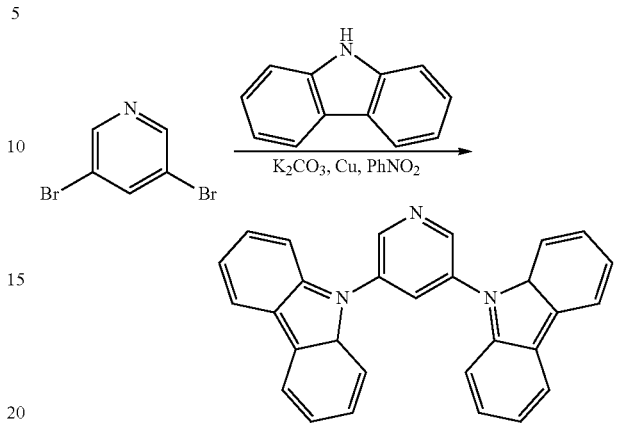

The ligand mCPy was synthesized by Ullmann reaction of carbazole and bromopyridine in the presence of Cu as catalyst. A mixture of carbazole (3.67 g, 22 mmol), 3,5-dibromopyridine (2.36 g, 10 mmol), potassium carbonate (3.04 g, 22 mmol), copper powder (0.6 g) and nitrobenzene (30 mL) was refluxed overnight. The mixture was then distilled at reduced pressure. The obtained residue was extracted with $CH_2Cl_2$ and purified by column chromatography on silica gel with hexane/$CH_2Cl_2$. The product was further purified by twice sublimation at low pressure ($10^{-5}$ torr). Total yield: 46%. $^1$H-NMR (500 MHZ, $CDCl_3$): 15 9.13 (br, 2H), 8.19 (s, 1H), 8.18 (d, J=8.0 Hz, 4H), 7.54 (d, J=8.5 Hz, 4H), 7.48 (t, J=7.5 Hz, 4H), 7.36 (t, J=7.5 Hz, 4H). Anal. Calcd. for $C_{29}H_{19}N_3$): C, 85.06; H, 4.68; N, 10.26. Found: C, 85.54; H, 4.52; N, 10.31. MS m/z: 4

TABLE 4

PLQYs and lifetimes of CuI:mCPy films with different ratios

| CuI:mCPy (molar ratio) | PLQY (%) | Lifetime (µS) |
| --- | --- | --- |
| 1.75:1 | 0 | — |
| 1.2:1 | 7.9 | 0.49, 3.0 |
| 1:2.3 | 48.2 | 3.1, 10.1 |
| 1:2.6 | 61.5 | 4.4, 12.8 |
| 1:3.7 | 63.3 | 3.4, 11.5 |
| 1:4.1 | 60.4 | 3.3, 11.0 |
| 1:5.5 | 63.9 | 3.5, 11.6 |

Figure 9:
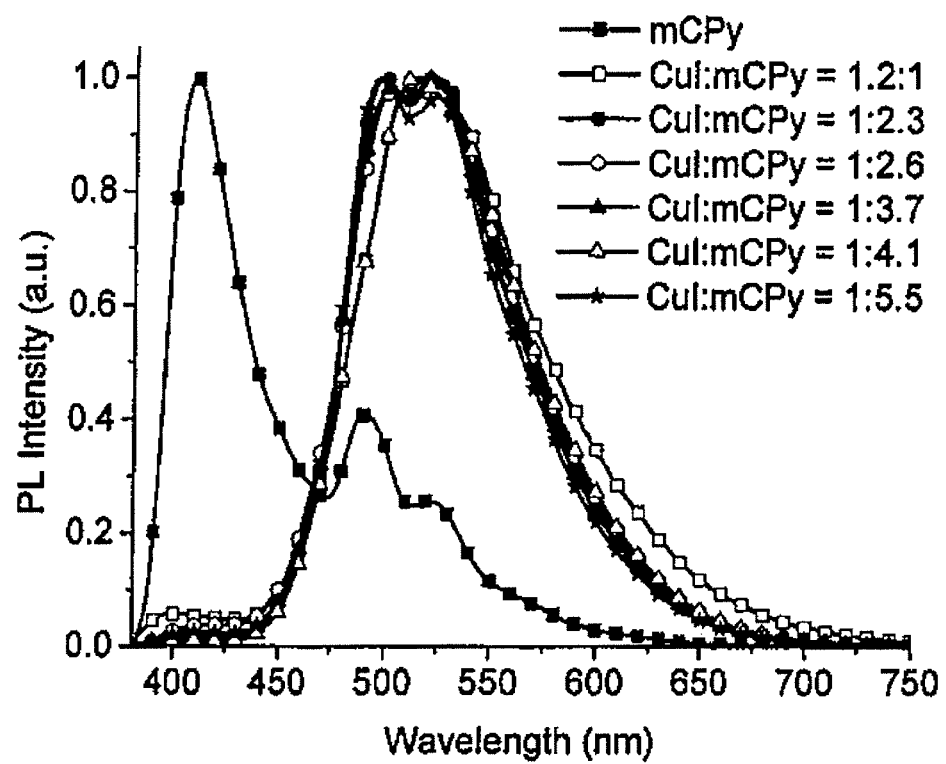
FIG. 9 shows the emission spectra of CuI:mCPy films with different molar ratios made by co-depositing CuI and mCPy in vacuum chamber.

FIG. 9 shows photoluminescent spectra of a series of CuI:mCPy films with different molar ratios made by co-depositing CuI and mCPy in vacuum chamber with two separate heating sources. By comparing the spectra of CuI:mCPy film and neat mCPy film, it is found that the CuI:mCPy film has almost pure emission from CuI:mCPy complex, which is different to CuI:TPBi and CuI:PBD films. Moreover, the maximum PLQY of the co-deposited CuI:mCPy film is up to 64%, indicating a promising candidate for OLEDs.

Figure 10:
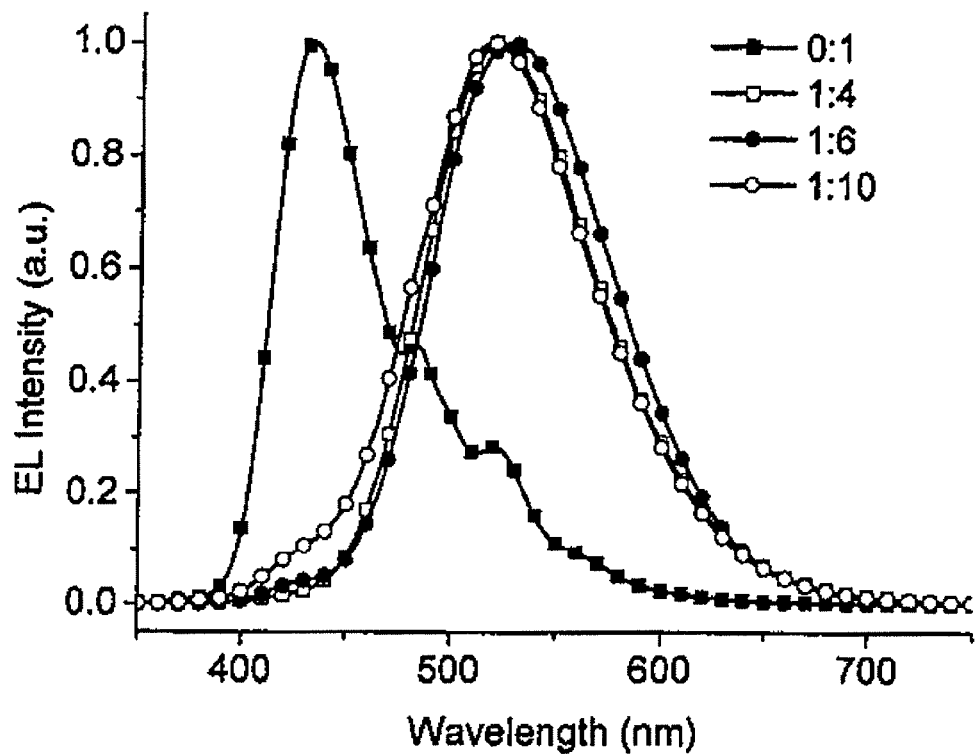
FIG. 10 shows the electroluminescent spectra of devices 1-4.
Figure 11:
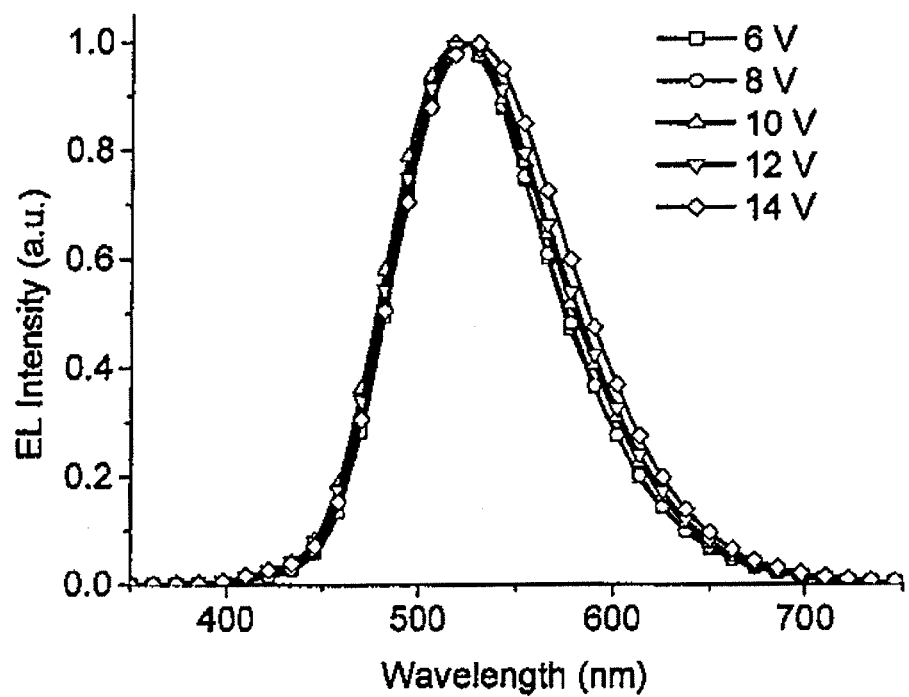
FIG. 11 shows the electroluminescent spectra of devices 1-4 at different voltages.

To apply CuI:mCPy in OLEDs, four devices ITO/NPD (250 Å)/CuI:mCPy (200 Å)/BCP (400 Å)/LiF (10 Å)/Al (1000 Å) were fabricated, where the molar ratio of CuI: mCPy films varies between 0:1 (device 1), 1:4 (device 2), 1:6 (device 3), and 1:10 (device 4). Table 5 provides device data. FIG. 10 shows electroluminescent spectra of the four devices at 8 V. The devices with CuI:mCPy complex have significantly different emission to that with neat mCPy, indicating the emission arises from CuI:mCPy complex, which consists with photoluminescent study. Moreover, identical pure CuI:mCPy complex emission was observed in the device 2 under different applied voltage (FIG. 11), which is different from devices with CuI:TPBi or CuI:PBO film as emission layer. The pure copper complex based electroluminescence demonstrated here suggests that the emission color of the co-deposited OLEDs could tuned by varying ligands.

Among the OLEDs with different molar ratios of CuI and mCPy, the device 4 shows the best EQE of 3.2%, and the maximum power efficiency (PE) and current efficiency (CE) are 3.2 μm/W and 5.9 cd/A, respectively. To get more information about OLEDs based on the co-deposited CuI:mCPy emission layer, another two devices ITO/NPD (250 Å)/CuI:mCPy (1:5, 200 Å)/BCPI Alq) (300 Å)/LiF (10 Å)/Al (1000 Å) were fabricated, where the thickness of BCP layer is 100 (device 5) or 0 Å (device 6). FIG. 12 shows electroluminescent spectra of devices 5 and 6 at 8 V. The two devices have same emission spectra, indicates that hole-electron combination occurs within CuI:mCPy layer and the electroluminescence is mainly come from CuI:mCPy complex. As summarized below in Table 5, the device 6 shows maximum EQE, PE, and CE of 4.4%, 6.9 μm/W and 8.2 cd/A, respectively. It has been improved as compared to those of the device 2, suggests that the device performance with co-deposited CuI:mCPy emission layer could be further improved by modifying device configuration.

TABLE 5

| Device | $V_{on}^a$ (V) | $L_{max}^b$ (cd/m$^2$) | $EQE_{max}$ (%) | $PE_{max}$ (lm/W) | $CE_{max}$ (cd/A) |
|---|---|---|---|---|---|
| 1 | 6.3 | 2785 | 0.52 | 0.45 | 0.97 |
| 2 | 3.7 | 5257 | 2.4 | 2.6 | 4.4 |
| 3 | 3.6 | 5778 | 3.0 | 3.0 | 5.6 |
| 4 | 3.8 | 5501 | 3.2 | 3.2 | 5.9 |
| 5 | 3.6 | 5706 | 3.9 | 7.1 | 7.3 |
| 6 | 3.7 | 5802 | 4.4 | 6.9 | 8.2 |

To understand the luminescent species in CuI:mCPy film we firstly co-deposited CuI and 1,3-bis(carbazol-9-yl)benzene (mCP) using the same technique to make CuI: mCPy films. FIG. 13 shows photoluminescent spectra of CuI:mCP film and neat mCP film. The CuI:mCP has identical emission spectrum to that of mCP, indicating that the pyridine-nitrogen is response for the emission species in CuI:mCPy film. Thus the luminescent species in CuI:mCPy film might be viewed as reaction products of CuI and pyridine ring. It should be noted that there are mainly three products [CuIpy]$_\infty$, Cu$_2$I$_2$(py)$_4$, and Cu$_4$I$_4$(py)$_4$ for the reaction of CuI and pyridine. They show blue, green, and orange emissions with maximum wavelength at 437, 517, and 580 nm in solid state at room temperature, respectively. [Kyle, K. R.; Ryu, C. K.; Dibenedetto, J. A.; Ford, P. C., *Journal of the American Chemical Society* 1991, 113, (8), 2954-2965.]

Secondly, a model complex A was synthesized by mixing solutions of 102 mg CuI in CH$_3$CN and 48 mg mCPy in CH$_2$Cl$_2$ at room temperature. Elemental analysis shows that the complex A has CuI:mCPy ratio of 1:1. The model complex A has blue emission with maximum wavelength around 480 nm (FIG. 14), likely to be [CuImCPy]$_n$. Moreover, the neat film of A and the film made by doping A in mCPy have nearly the same emission spectra to that of the co-deposited CuI:mCPy film. This suggests that the complex A might be responsible for the luminescence observed in CuI:mCPy film.

Another model complex B was also synthesized by adding small amount of CuI in CH$_3$CN to excess of mCPy in CH$_2$Cl$_2$. The complex B was obtained as white crystals with green emission. Single X-ray diffraction measurement indicates that the model complex B has structure of Cu$_4$I$_4$(mCPy$_4$).3CH$_2$Cl$_2$ (FIG. 15). This means that even with a cubane structure that mostly reported as yellow to red emitter [Kyle, K. R.; Ryu, C. K.; Dibenedetto, J. A.; Ford, P. C., *Journal of the American Chemical Society* 1991, 113, (8), 2954-2965], the complex Cu$_4$I$_4$(mCPy$_4$) may be a green emitter and responsible for the luminescent in CuI:mCPy film.

Although model complex with structure of Cu$_2$I$_2$(mCPy)$_4$ has not been synthesized yet, it is possible that there is such structure in co-deposited CuI:mCPy film, since Cu$_2$I$_2$(mCPy)$_4$ is well known as a green material and theoretically Cu$_2$I$_2$(mCPy)$_4$ may have green emission that similar to the CuI:mCPy film. In support of this assignment for the emitting species is the fact that the thin film PL efficiency is highest for CuI:mCPy ratios of 1:2 or higher (in mCPy), see Table 4. Less than 2 equivalents of mCPy per CuI is not likely to give Cu$_2$I$_2$(mCPy)$_4$ efficiently.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A method, comprising:
    co-depositing one or more metal complexes having the formula MX$_n$ and one or more ligands by thermal vacuum depositing from two different heating sources to form a film comprising a phosphorescent complex over a substrate,
    wherein M is a transition metal or lanthanide;
    wherein X is alkyl, aryl, F, Cl, Br, I, SCN, OCN, CN, OR, and SR or combinations thereof;
    wherein ft is alkyl or aryl;
    wherein n is 1-10;
    wherein each ligand is independently a mono-, di-, tri- or polydentate ligand; and
    wherein the co-depositing step forms in-situ a phosphorescent complex comprising two to six of the metal complexes having the formula MX$_n$ and the one or more ligands.

2. The method of claim 1, wherein at least one ligand is a neutral ligand that is coordinated to the M through a C, N, O, P or S atom.

3. The method of claim 2, wherein at least one ligand is a neutral ligand that is coordinated to the M through a N atom.

4. The method of claim 1, wherein the phosphorescent complex is selected from the group consisting of:

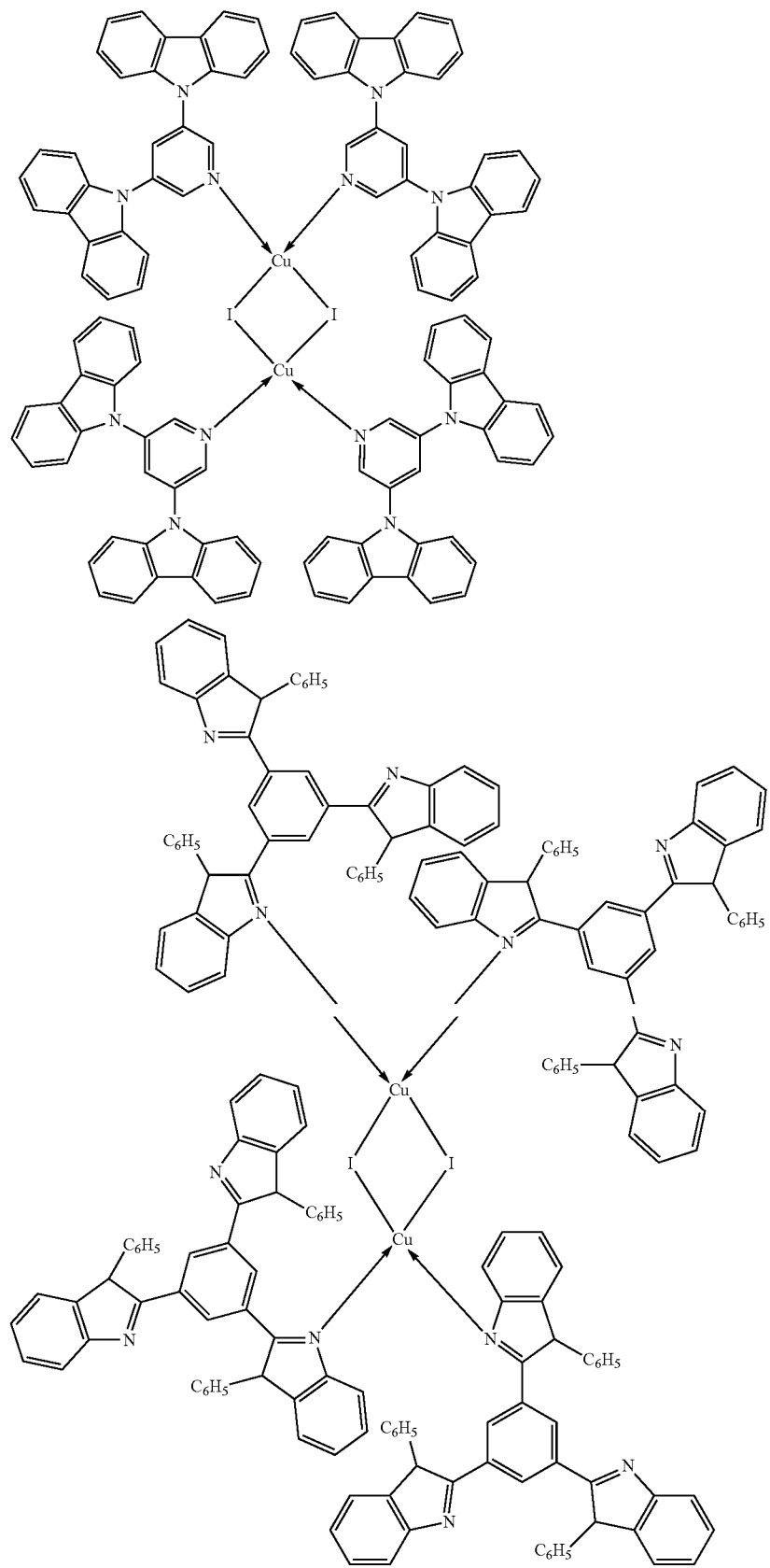

-continued

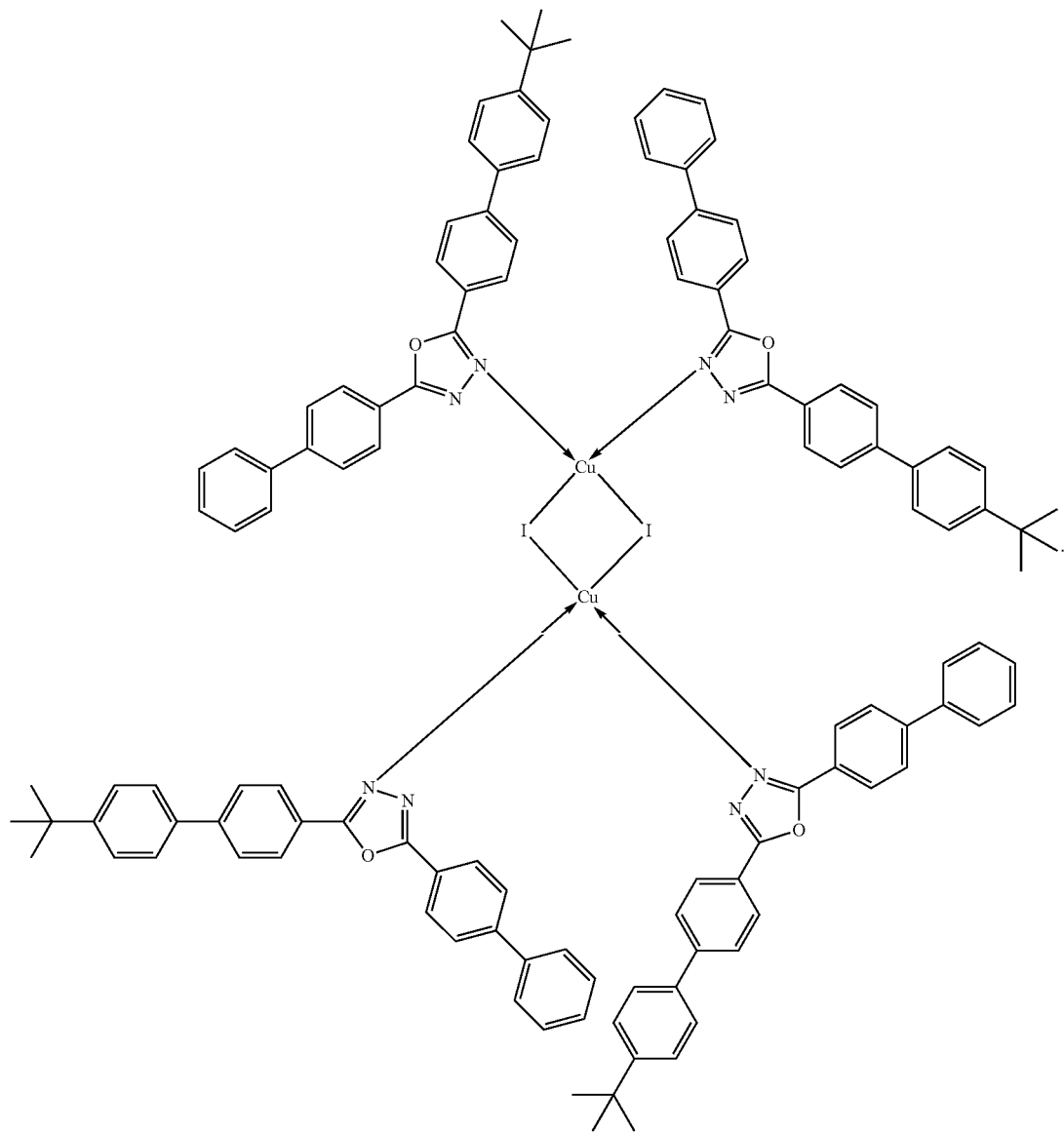

5. The method of claim 1, wherein the phosphorescent complex is homoleptic.

6. The method of claim 1, wherein the phosphorescent complex is heteroleptic.

7. A method, comprising:
co-depositing one or more metal complexes having the formula $MX_n$ and one or more ligand by thermal vacuum depositing from two different heating sources to form a film comprising a phosphorescent complex over a substrate,
wherein M is copper (I);
wherein X is alkyl, aryl, F, Cl, Br, I, SCN, OCN, CN, OR, and SR or combinations thereof;
wherein R is alkyl or aryl;
wherein n is 1-10;
wherein each ligand is independently a mono-, di-, tri- or polydentate ligand;
wherein one to six of the metal complexes having the formula $MX_n$ and the more than one ligands react in situ during the co-depositing step and form the phosphorescent complex.

8. The method of claim 7, wherein the metal complex is CuI.

9. The method of claim 7, wherein n is 1-3.

10. The method of claim 7, wherein the phosphorescent complex includes 2 of the metal complexes.

11. The method of claim 7, wherein each ligand is a neutral ligand that is coordinated to the copper (I) through a C, N, O, P or S atom.

12. The method of claim 11, wherein each ligand is a neutral ligand that is coordinated to the copper (I) through a N atom.

13. The method of claim 7, wherein at least one ligand is selected from the group consisting of:

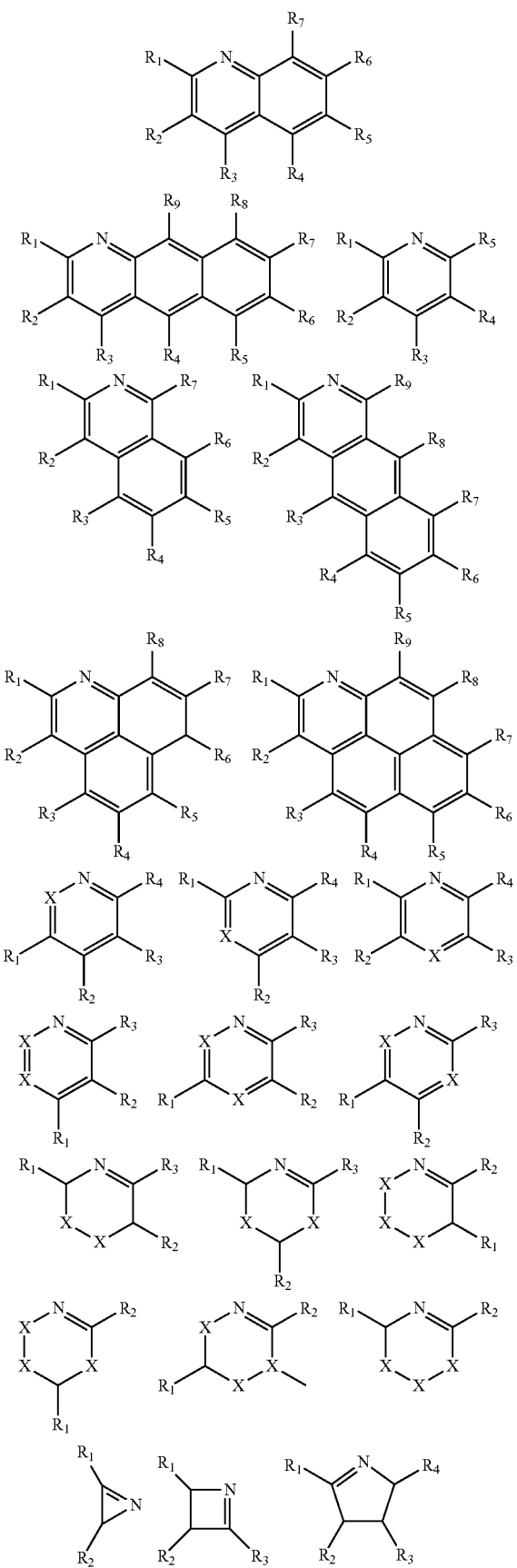

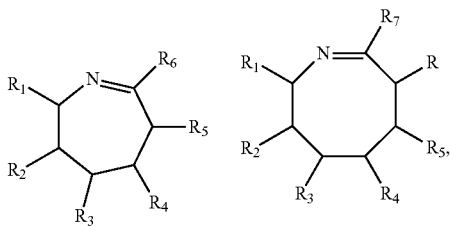

wherein X is S, O, NR;

wherein R, $R_1$, $R_2$, $R_3$, $R_4$, $R_5$, $R_6$, $R_7$, $R_8$ and $R_9$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein the ligand is coordinated to the copper (I) via at least one atom of the ligand.

14. The method of claim 13, wherein at least one ligand is selected from the group consisting of:

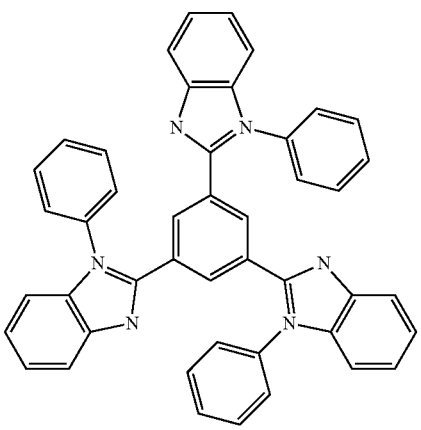

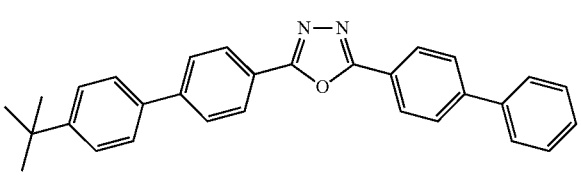

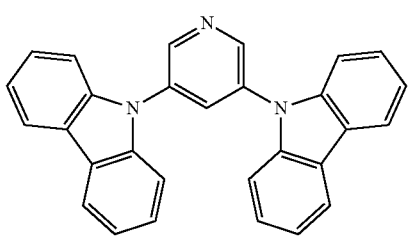

-continued

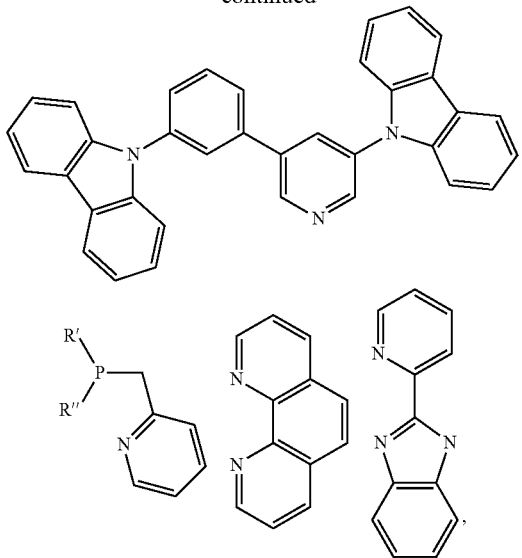

wherein R' and R" are independently selected from the group consisting of hydrogen, deuterium, halide, alkyl, cycloalkyl, heteroalkyl, arylalkyl, alkoxy, aryloxy, amino, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

15. The method of claim 7, wherein at least one ligand is a charged ligand having the formula:

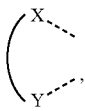

wherein Y and X are independently selected from the group consisting of C, N, O, P and S.

16. The method of claim 15, wherein

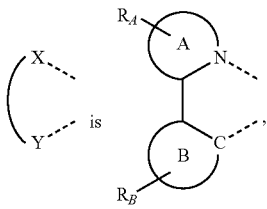

wherein A and B are each independently a 5 or 6-membered aromatic or heteroaromatic ring;
wherein A-B represents a bonded pair of aromatic or heteroaromatic rings coordinated to the metal via a nitrogen atom on ring A and an $sp^2$ hybridized carbon atom on ring B;
wherein each of $R_A$ and $R_B$ may represent mono, di, tri, or tetra substituents;
wherein each of $R_A$ and $R_B$ substituents are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

17. The method of claim 7, further comprising:
providing a first electrode disposed over the substrate before the co-depositing step; and
depositing a second electrode over the co-deposited film of phosphorescent complex.

18. The method of claim 17, wherein the first electrode is an anode and the second electrode is a cathode.

19. The method of claim 7, wherein the phosphorescent complex is homoleptic.

20. The method of claim 7, wherein the phosphorescent complex is heteroleptic.

* * * * *

UNITED STATES PATENT AND TRADEMARK OFFICE
CERTIFICATE OF CORRECTION

PATENT NO. : 9,435,021 B2
APPLICATION NO. : 13/193036
DATED : September 6, 2016
INVENTOR(S) : Mark E. Thompson et al.

It is certified that error appears in the above-identified patent and that said Letters Patent is hereby corrected as shown below:

In the Specification

In Column 5, Line 18, delete "sulfonyl" and insert -- sulfinyl --

In Column 15, Line 6, delete "sulfonyl" and insert -- sulfinyl --

In Column 23, Line 44, delete "oxadiazole" and insert -- oxatriazole --

In the Claims

In Claim 1, Column 94, Line 50, delete "ft" and insert -- R --

Signed and Sealed this
Second Day of May, 2017

Michelle K. Lee
*Director of the United States Patent and Trademark Office*